(12) United States Patent
Blumenkopf et al.

(10) Patent No.: US 7,265,221 B2
(45) Date of Patent: *Sep. 4, 2007

(54) PYRROLO[2,3-D]PYRIMIDINE COMPOUNDS

(75) Inventors: Todd A. Blumenkopf, Old Lyme, CT (US); Mark E. Flanagan, Gales Ferry, CT (US); Michael J. Munchhof, Salem, CT (US)

(73) Assignee: Pfizer, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/474,233

(22) Filed: Jun. 23, 2006

(65) Prior Publication Data

US 2006/0241131 A1 Oct. 26, 2006

Related U.S. Application Data

(60) Continuation of application No. 11/211,217, filed on Aug. 24, 2005, now Pat. No. 7,091,208, which is a division of application No. 10/640,227, filed on Aug. 13, 2003, now Pat. No. 6,956,041, which is a continuation of application No. 09/732,669, filed on Dec. 8, 2000, now Pat. No. 6,627,754.

(60) Provisional application No. 60/170,179, filed on Dec. 10, 1999.

(51) Int. Cl.
*C07D 487/04* (2006.01)
*A61K 31/519* (2006.01)
*A61P 11/06* (2006.01)
*A61P 19/02* (2006.01)
*A61P 35/02* (2006.01)

(52) U.S. Cl. .................. 544/280; 514/265.1
(58) Field of Classification Search ............ 544/280
See application file for complete search history.

(56) References Cited

U.S. PATENT DOCUMENTS

| | | | | |
|---|---|---|---|---|
| 3,037,980 A | 6/1962 | Hitchings et al. | ......... | 260/256.4 |
| 5,389,509 A | 2/1995 | Maskasky | ......... | 430/567 |
| 5,496,946 A | 3/1996 | Akimoto et al. | ......... | 544/321 |
| 5,686,457 A | 11/1997 | Traxler et al. | ......... | 514/258 |
| 6,080,747 A | 6/2000 | Uckun et al. | ......... | 514/259 |
| 6,136,595 A | 10/2000 | Ihle et al. | ......... | 435/320.1 |
| 6,180,636 B1 | 1/2001 | Traxler et al. | ......... | 514/258 |
| 6,187,552 B1 | 2/2001 | Roberds et al. | ......... | 435/7.93 |
| 6,310,063 B1 | 10/2001 | Ge et al. | ......... | 514/234.5 |
| 6,610,847 B2 | 8/2003 | Blumenkopf et al. | ......... | 544/280 |
| 6,627,754 B2 * | 9/2003 | Blumenkopf et al. | ......... | 544/280 |
| 6,635,762 B1 | 10/2003 | Blumenkopf et al. | ......... | 544/280 |
| 6,696,567 B2 | 2/2004 | Blumenkopf et al. | ......... | 544/280 |
| 6,890,929 B2 | 5/2005 | Blumenkopf et al. | ......... | 514/258 |
| 6,956,041 B2 * | 10/2005 | Blumenkopf et al. | ......... | 514/258.1 |
| 6,962,993 B2 | 11/2005 | Blumenkopf et al. | ......... | 544/280 |
| 6,965,027 B2 | 11/2005 | Flanagan et al. | ......... | 544/280 |
| 7,079,208 B2 | 7/2006 | Kim et al. | ......... | 349/119 |

| | | | |
|---|---|---|---|
| 2003/0073719 A1 | 4/2003 | Flanagan | |
| 2004/0058922 A1 | 3/2004 | Blumenkopf | |
| 2004/0229923 A1 | 11/2004 | Wilcox | |
| 2005/0159434 A1 | 7/2005 | Flanagan | |
| 2005/0171128 A1 | 8/2005 | Blumenkopf | |
| 2005/0197349 A1 | 9/2005 | Blumenkopf | |

FOREIGN PATENT DOCUMENTS

| | | |
|---|---|---|
| EP | 0334636 | 9/1989 |
| EP | 0795556 | 9/1997 |
| EP | 0682027 | 10/1997 |
| GB | 0915303 | 1/1963 |
| WO | WO9519774 | 7/1995 |
| WO | WO9802438 | 7/1996 |
| WO | WO9640142 | 12/1996 |
| WO | WO9702262 | 1/1997 |
| WO | WO9702266 | 1/1997 |
| WO | WO9713771 | 4/1997 |
| WO | WO9718212 | 5/1997 |

(Continued)

OTHER PUBLICATIONS

Baird, A.M., et al., *J. Leukocyte Biology*, "T Cell Development and Activation in JAK-3-Deficient Mice", vol. 63, pp. 669-672 (1998).

(Continued)

*Primary Examiner*—Venkataraman Balasubramanian
(74) *Attorney, Agent, or Firm*—Christopher Verni; Gregg Benson

(57) ABSTRACT

A compound of the formula

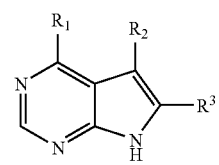

wherein $R^1$, $R^2$ and $R^3$ are as defined above, which are inhibitors of the enzyme protein kinases such as Janus Kinase 3 and as such are useful therapy as immunosuppressive agents for organ transplants, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other autoimmune diseases.

18 Claims, No Drawings

FOREIGN PATENT DOCUMENTS

| | | |
|---|---|---|
| WO | WO9727199 | 7/1997 |
| WO | WO9728161 | 8/1997 |
| WO | WO9732879 | 9/1997 |
| WO | WO9749706 | 12/1997 |
| WO | WO9802437 | 1/1998 |
| WO | WO9807726 | 2/1998 |
| WO | WO9823613 | 6/1998 |
| WO | WO9833798 | 8/1998 |
| WO | WO9951599 | 10/1999 |
| WO | WO9961428 | 12/1999 |
| WO | WO9965908 | 12/1999 |
| WO | WO9965909 | 12/1999 |
| WO | WO0000202 | 1/2000 |
| WO | WO0010981 | 3/2000 |
| WO | WO0017203 | 3/2000 |
| WO | WO0142246 | 6/2001 |
| WO | WO0200661 | 1/2002 |

OTHER PUBLICATIONS

Candotti, F., et al., *Springer Semin. Immunopathology*, "Severe Combined Immune Deficiencies due to Defects in the Common γ chain-JAK3 Signaling Pathway", vol. 19, pp. 401-415 (1998).

Chen, E., et al., *Transplantation Proceedings*, "Advances in Cytokine Signaling: The Role of JAKs and STATs", vol. 31, pp. 1482-1487 (1999).

Eynon, E.E., et al., *Journal of Interferon and Cytokine Research*, "Disruption of Cytokine Signaling in Lymphoid Development: Unique Contributions of the Common Cytokine Gamma Chain and the JAK3 Kinase", vol. 16, pp. 667-684 (1996).

Ghosh, S., et al., *Acta Crystallogr,.C:Crystal. Structure Commun.*, "4-[(3-Bromo-4-hydroxyphenyl)amino]6,7-dimethoxyquinazolin-1-ium Chloride Methanol Solvate and 4-[(3-hydroxyphenyl)amino0-6,7-dimethoxy-1-quinazolinium Chloride", vol. C57, pp. 76-78 (2001).

Hanke, J.H., et al., *Inflammation Research*, "Role of Tyrosine Kiniases in Lymphocyte Activation: Targets for Drug Intervention", vol. 44, pp. 357-371 (1995).

Ihle, J.N., *Advance Immunology*, "The Janus Protein Tyrosine Kinase Family and Its Role in Cytokine Signaling", vol. 60, p. 1-35 (1995).

Ihle, J.N., *Semin. Immunology*, "The Janus Protein Tyrosine Kinases in Hematopoietic Cytokine Signaling", vol. 7, p. 247 (1995).

Kirken, R.A., et al., *Cytokine*, "Activation of JAK3, but not JAK1, is Critical for IL-2-Induced Proliferation and Stat 5 Recruitment by a Cooh-Terminal Region of IL-2 Receptor β-Chain", vol. 7, pp. 689-700 (1995).

Liu, K.D., et al., *Current Opinion of Immunology*, "JAK/STAT Signaling By Cytokine Receptors", vol. 10, pp. 271-278 (1998).

Li, X.C., et al., *Journal of Immunology*, "Blocking the Common γ-Chain of Cytokine Receptors Induces T Cell Apoptosis and Long-term Islet Allograft Survival", vol. 164, pp. 1193-1199 (2000).

Leonard, W.J., et al., *Annual Review of Immunology*, "JAKS and STATS: Biological Implications", vol. 16, pp. 293-322 (1998).

Malaviya, R., et al., *J. Pharmacology and Experimental Therapeutics*, "Treatment of Allergic Asthma by Targeting Janus Kinase 3-Dependent Leukotriene Synthesis in Mast Cells with 4-(3-hydroxyphenyl)amino-6,7-dimethoxyquinazoline (WHI-P97)", vol. 295, No. 3 pp. 912-926 (2000).

Malaviya, R., et al., *Biochemical and Biophysical Research Communications*, "Genetic and Biochemical Evidence for a Critical Role of Janus Kinase (JAK)-3 in Mast Cell-Mediated Type 1 Hypersensitivity Reactions", vol. 257, pp. 807-813 (1999).

Malaviya, R., et al., *Journal of Biological Chemistry*, "Targeting Janus Kinase 3 in Mast Cells Prevents Immediate Hypersensitivity Reactions and Anaphylaxis", vol. 274(38), pp. 27028-27038 (1999).

Malabarba, M.G., et al., *Journal of Biological Chemistry*, "Activation of JAK3, but not JAK1, is Critical to Interleukin-4(IL4) Stimulated Proliferation and Requires a Membrane-Proximal Region of IL4 Receptor α", vol. 270(16), pp. 9630-9637 (1995).

Moriggi, R., et al., *Immunity*, "Stat5 Activation is Uniquely Associated with Cytokine Signaling in Peripheral T Cells", vol. 11, pp. 225-230 (1995).

Musso, T., et al., *Journal of Experimental Medicine*, "Regulation of JAK3 Expression in Human Monocytes: Phosphorylation in Response to Interleukins 2, 4, and 7", vol. 181, pp. 1425-1431 (1995).

Nelson, B.H., et al., *Proceedings of National Academy of Science USA*, "Requirement for an Initial Signal from the Membrane-Proximal Region of the Interleukin 2 Receptor $\gamma_c$ chain for Janus Kinsase Activation Leading to T Cell Proliferation", vol. 94, pp. 1878-1883 (1997).

Notarangelo, L.D., et al., *Progressive in Immunodeficiency*, "Severe Combined Immune Deficiency due to Defects of the JAK3 Tyrosine Kinase", vol. 6, pp. 61-68 (1996).

Oakes, S.A., et al., *Immunity*, "Signaling via IL-2 and IL-4 in JAK3-Deficient Severe Combined Immunodeficiency Lymphocytes: JAK3-Dependent and Independent Pathways", vol. 5, pp. 605-615 (1996).

O'Shea, J.J., et al., *Nature*, "Phosphorylation and Activation of the JAK-3 Janus Kinase in Response to Interleukin-2", vol. 370(14), pp. 151-153 (1994).

Russell, S.M., et al., *Science*, "Interaction of IL-2Rβ and $\gamma_c$ Chains with JAK1 and JAK3: Implications for XSCID and XCID", vol. 266, pp. 1042-1045 (1994).

Sudbeck, E.A., et al., *Clinical Cancer Research*, "Structure-based Design of Specific Inhibitors of Janus Kinase 3 as Apoptosis-Inducing Antileukemic Agents", vol. 5, pp. 1569-1582 (1999).

Sudbeck, E.A., et al., *IDrugs*, "Recent Advances in JAK3 Kinase Inhibitors", vol. 2(10), pp. 1026-1030 (1999).

Sudbeck, E.A., et al., *Acta Cyrstallogr., SectC: Crystal Structure Communications* "An Inhibitor of Janus Kinase 3: 4-(4-hydroxyphenynlamino)-6,7-dimethoxyquinazolin-1-ium chloride methanol solvate", vol. C56, pp. 1282-1283 (2000).

Thomis, D.C., et al., *The Journal of Immunology*, "The JAK Family Tyrosine Kinase JAK3 is Required for IL-2 Synthesis by Naïve/Resting CD4+ T Cells", vol. 163, pp. 5411-5417 (1999).

Thomis, D.C., et al., *Journal of Experimental Medicine*, "Peripheral Expression of JAK3 is Required to Maintain T Lymphocyte Function", vol. 185(2), pp. 197-206 (1997).

Traxler, et al., *Expert Opinion on Therapeutic Patents.*, "Protein Tyrosine Kinase Inhibitors in Cancer Treatment", vol. 7(6), pp. 571-588 (1997).

Traxler, et al., *J. Med. Chem.*, "4-(Phenylamino)pyrrolopyrimidines: Potent and Selective, ATP Site Directed Inhibitors of the EGF-Receptor Protein Tyrosine Kinase", vol. 39, pp. 2285-2292 (1996).

Trieu, V.N., et al., *Biochemical and Biophysical Research Communications*, "A Specific Inhibitor of Janus Kinase-3 Increases Survival in a Transgenic Mouse Model of Amyotrophic Lateral Sclerosis", vol. 267, pp. 22-25 (2000).

Uckun, F.M., et al., *Clinical Cancer Research*, "In Vivo Toxicity and Pharmacokinetic Features of the Janus Kinase 3 Inhibitor WHI-P131 [4-(4'-Hydroxyphenyl)-Amino-6,7-Dimethoxyquinazoline]", vol. 5, pp. 2954-2962 (1999).

Wang, L.H., et al., *Journal of Immunology*, "JAK3, STAT, and MAPK Signaling Pathways as Novel Molecular Targets for the Tyrphostin AG-490 Regulation of IL-2-Mediated T Cell Response", vol. 162, pp. 3897-3904 (1999).

U.S. Appl. No. 09/335,121, filed Jun. 17, 1999 Todd A. Blumenkopf.

U.S. Appl. No. 10/640,079, filed Aug. 13, 2003 Todd A. Blumenkopf.

\* cited by examiner

PYRROLO[2,3-D]PYRIMIDINE COMPOUNDS

This application is a continuation of U.S. Patent Application No. 11/211,217 filed Aug. 24, 2005, now issued as U.S. Pat. No. 7,091,208, which is a divisional of U.S. patent application Ser. No. 10/640,227 filed Aug. 13, 2003, now issued as U.S. Pat. No. 6,956,041, which in turn is a continuation of U.S. patent application Ser. No. 09/732,669 filed Dec. 8, 2000, now issued as U.S. Pat. No. 6,627,754, which in turn claims the benefit of priority under 35 U.S.C. § 119(e) of U.S. Provisional Patent Application No. 60/170,179 filed Dec. 10, 1999, all of which are hereby incorporated herein by reference for all purposes.

BACKGROUND OF THE INVENTION

The present invention relates to pyrrolo[2,3]pyrimidine compounds which are inhibitors of protein kinases, such as the enzyme. Janus Kinase 3 (hereinafter also referred to as JAK3) and as such are useful therapy as immunosuppressive agents for organ transplants, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

This invention also relates to a method of using such compounds in the treatment of the above indications in mammals, especially humans, and the pharmaceutical compositions useful therefor. JAK3 is a member of the Janus family of protein kinases. Although the other members of this family are expressed by essentially all tissues, JAK3 expression is limited to hematopoetic cells. This is consistent with its essential role in signaling through the receptors for IL-2, IL-4, IL-7, IL-9 and IL-15 by non-covalent association of JAK3 with the gamma chain common to these multichain receptors. XSCID patient populations have been identified with severely reduced levels of JAK3 protein or with genetic defects to the common gamma chain, suggesting that immunosuppression should result from blocking signaling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

SUMMARY OF THE INVENTION

The present invention relates to a compound of the formula

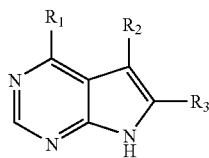

I or the pharmaceutically acceptable salt thereof; wherein $R^1$ is a group of the formula

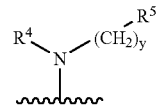

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is $(C_2-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy $(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $(C_1-C_6)$alkyl-S(O)$_m$, $R^{15}R^{16}NS(O)_m$, $R_{15}R^6NS(O)_m(C_1-C_6)$alkyl, $R^{15}S(O)_m R^{16}N$, $R^{15}S(O)_m R^{16}N(C_1-C_6)$alkyl wherein m is 0, 1 or 2 and $R^{15}$ and $R^{15}$ are each independently selected from hydrogen or $(C_1-C_6)$alkyl; or a group of the formula

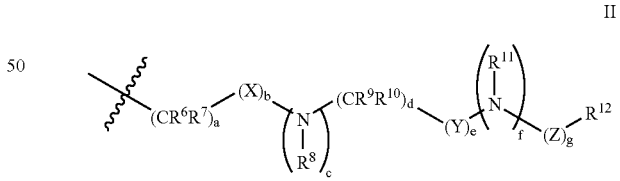

II wherein a is 0, 1, 2, 3 or 4;

b, c, e, f and g are each independently 0 or 1;

d is 0, 1, 2, or 3;

X is $S(O)_n$ wherein n is 0, 1 or 2; oxygen, carbonyl or —C(=N-cyano)—;

Y is $S(O)_n$ wherein n is 0, 1 or 2; or carbonyl; and

Z is carbonyl, C(O)O—, C(O)NR— or $S(O)_n$ wherein n is 0, 1 or 2;

$R^6$, $R^7$, $R^8$, $R^9$, $R^{10}$ and $R^{11}$ are each independently selected from the group consisting of hydrogen or $(C_1-C_6)$ alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$ amino, amino$(C_1-C_6)$alkyl, $(C_1-C_6)$alkoxy-CO—NH, $(C_1-C_6)$alkylamino-CO—, $(C_1-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-S(O)$_m$, $(C_1-C_6)$alkyl-S(O)$_m$—$(C_1-C_6)$alkyl, $R^{15}R^{16}NS(O)_m$, $R^{15}R^{16}NS(O)_m$ $(C_1-C_6)$alkyl, $R^{15}S(O)_m$ $R^{16}N$, $R^{15}S(O)_m R^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each independently selected from the group consisting of hydrogen, deuterium, amino, halo, hydoxy, nitro, carboxy, $(C_2-C_6)$alkenyl, $(C_2-C_6)$alkynyl, trifluoromethyl, trifluoromethoxy, $(C_1-C_6)$alkyl, $(C_1-C_6)$alkoxy, $(C_3-C_{10})$cycloalkyl wherein the alkyl, alkoxy or cycloalkyl groups are optionally substituted by one to three groups selected from halo, hydroxy, carboxy, amino$(C_1-C_6)$alkylthio, $(C_1-C_6)$alkylamino, $((C_1-C_6)$alkyl$)_2$amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl$)_2$amino, $(C_6-C_{10})$arylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkyamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy$(C_1-C_6)$alkoxy, benzyloxycarbonyl$(C_1-C_6)$alkoxy, $(C_1-C_6)$alkoxycarbonyl$(C_1-C_6)$alkyl, $(C_6-C_{10})$aryl, amino, amino$(C_1-C_6)$alkyl, $(C_1-C_6)$alkoxycarbonylamino, $(C_6-C_{10})$aryl$(C_1-C_6)$alkoxycarbonylamino, $(C_1-C_6)$alkylamino, $((C_1-C_6)$alkyl$)_2$amino, $(C_1-C_6)$alkylamino$(C_1-C_6)$alkyl, $((C_1-C_6)$alkyl$)_2$amino$(C_1-C_6)$alkyl, hydroxy, $(C_1-C_6)$alkoxy, carboxy, carboxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxy-CO—NH—, $(C_1-C_6)$alkyl-CO—NH—, cyano, $(C_5-C_9)$heterocloalkyl, amino-CO—NH—, $(C_1-C_6)$alkylamino-CO—NH—, $((C_1-C_6)$alkyl$)_2$amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$alkyl$)_2$amino-CO—NH—$(C_1-C_6)$alkyl, $(C_6-C_{10})$arylamino CO—NH—$(C_1-C_6)$alkyl, $(C_5-C_9)$heteroarylamino-CO—NH—$(C_1-C_6)$alkyl, $(C_1-C_6)$alkylsulfonyl, $(C_1-C_6)$alkylsulfonylamino, $(C_1-C_6)$alkylsulfonylamino$(C_1-C_6)$alkyl, $(C_6-C_{10})$arylsulfonyl, $(C_6-C_{10})$arylsulfonylamino, $(C_6-C_{10})$arylsulfonylamino$(C_1-C_6)$alkyl, $(C_1-C_6)$alkylsulfonylamino, $(C_1-C_6)$alkylsulfonylamino$(C_1-C_6)$alkyl, $(C_5-C_9)$heteroaryl or $(C_2-C_9)$heterocycloalkyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The term "alkyl", as used herein, unless otherwise indicated, includes saturated monovalent hydrocarbon radicals having straight or branched moieties or combinations thereof.

The term "alkoxy", as used herein, includes O-alkyl groups wherein "alkyl" is defined above.

The term "halo", as used herein, unless otherwise indicated, includes fluoro, chloro, bromo or iodo.

The compounds of this invention may contain double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (alkoxy), may be linear or branched, and they may also be cyclic (e, cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

$(C_2-C_9)$Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl; 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said $(C_2-C_9)$heterocycloalkyl rings is through a carbon or a $sp^3$ hybridized nitrogen heteroatom.

$(C_2-C_9)$Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said $(C_2-C_9)$heterocycloalkyl rings is through a carbon atom or a $sp^3$ hybridized nitrogen heteroatom.

$(C_6-C_{10})$aryl when used herein refers to phenyl or naphthyl.

Compounds of formula (I) may be administered in a pharmaceutically acceptable form either alone or in combination with one or more additional agents which modulate a mammalian immune system or with antiinflammatory agents. These agents may include but are not limited to cyclosporin A (e.g. Sandimmune® or Neoral®, rapamycin, FK-506 (tacrolimus), leflunomide, deoxyspergualin, mycophenolate (e.g. Cellcept®), azathioprine (e.g. Imuran®), daclizumab (e.g. Zenapax®). OKT3 (e.g. Orthoclone®), AtGam, aspirin, acetaminophen, ibuprofen, naproxen, piroxicam, and antiinflammatory steroids (e.g. prednisolone or dexamethasone). These agents may be administered as part of the same or separate dosage forms, via the same or different routes of administration, and on the same or different administration schedules according to standard pharmaceutical practice.

The compounds of this invention include all conformational isomers (e.g., cis and trans isomers. The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations. The compounds of formula I may also exist as tautomers. This invention relates to the use of all such tautomers and mixtures thereof.

This invention also encompasses pharmaceutical compositions containing prodrugs of compounds of the formula I. This invention also encompasses methods of treating or preventing disorders that can be treated or prevented by the inhibition of protein kinases, such as the enzyme Janus Kinase 3 comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of formula I through the carbonyl carbon prodrug sidechain.

Preferred compounds of formula I include those wherein a is 0; b is 1; X is carbonyl; c is 0; d is 0; e is 0; f is 0; and g is 0.

Other preferred compounds of formula I include those wherein a is 0; b is 1; X is carbonyl; c is 0; d is 1; e is 0; f is 0, and g is 0.

Other preferred compounds of formula I include those wherein a is 0; b is 1; X is carbonyl; c is 1; d is 0; e is 0; f is 0; and g is 0.

Other preferred compounds of formula I include those wherein a is 0; b is 1; X is —C(=N=cyano)-; c is 1; d is 0; e is 0; f is 0; and g is 0.

Other preferred compounds of formula I include those wherein a is 0; b is 0; c is 0; d is 0; e is 0; f is 0; g is 1; and Z is —C(O)—O—.

Other preferred compounds of formula I include those wherein a is 0; b is 1; X is $S(O)_n$; n is 2; c is 0; d is 0; e is 0; f is 0; and g is 0.

Other preferred compounds of formula I include those wherein a is 0; b is 1; X is $S(O)_n$; n is 2; c is 0; d is 2; e is 0; f is 1; g is 1; and Z is carbonyl.

Other preferred compounds of formula I include those wherein a is 0; b is 1; X is $S(O)_n$; n is 2; c is 0; d is 2; e is 0; f is 1; and g is 0.

Other preferred compounds of formula I include those wherein a is 0; b is 1; X is carbonyl; c is 1; d is 0; e is 1; Y is $S(O)_n$; n is 2; f is 0; and g is 0.

Other preferred compounds of formula I include those wherein a is 0; b is 1; X is $S(O)_n$; is 2; c is 1; d is 0; e is 0; f is 0; and g is 0.

Other preferred compounds of formula I include those wherein a is 1; b is 1; X is carbonyl; cis 1; d is 0; e is 0; f is 0; and g is 0.

Other preferred compounds of formula I include those wherein a is 0; b is 1; X is $S(O)_n$; c is 6; d is 1; e is 1; Y is $S(O)_n$; n is 2; f is 0; and g is 0.

Other preferred compounds of formula I include those wherein a is 0; b is 1; X is $S(O)_n$; c is 0; d is 1; e is 1; Y is $S(O)_n$; n is 2; f is 1; and g is 0.

Other preferred compounds of formula I include those wherein a is 0; b is 1; X is oxygen; c is 0; d is 1; e is 1; Y is $S(O)_n$; n is 2; f is 1; and g is 0.

Other preferred compounds of formula I include those wherein a is 0; b is 1; X is oxygen; c is 0; d is 1; e is 1; Y is $S(O)_n$; n is 2; f is 0; and g is 0.

Other preferred compounds of formula I include those wherein a is 0; b is 1; X is carbonyl; c is 1; d is 1; e is 1; Y is $S(O)_n$; f is 0; and g is 0.

Other preferred compounds of formula I include those wherein a is 0; b is 1; X is carbonyl; c is 1; d is 1; e is 1; Y is $S(O)_n$; n is 2; f is 1; and g is 0.

Other preferred compounds of formula I include those wherein $R^{12}$ is cyano, trifluoromethyl, $(C_1-C_6)$alkyl, trifluoromethyl$(C_1-C_6)$alkyl, $(C_1-C_6)$alkylamino, $((C_1-C_6)$alkyl$)_2$amino, $(C_2-C_6)$alkynyl, cyano$(C_1-C_6)$alkyl, $(C_1-C_6)$alkyl-S$(O)_m$ wherein m is 0, 1 or 2.

Specific preferred compounds of formula I include those wherein said compound is selected from the group consisting of:

Methyl-[4-methyl-1-(propane-1-sulfonyl)-piperidin-3-yl]-(7H-pyrrolo[2,3-d]pyrimidin-4-yl)-amine;

4-Methyl-3-[methyl-(7H-pyrrolo[2,3-d]pyrimidin-4-yl)-amino]-piperidine-1-carboxylic acid methyl ester;

3,3,3-Trifluoro-1-{4-methyl-3-[methyl-(7H-pyrrolo[2,3-d]pyrimidin-4-yl)-amino]-piperidin-1-yl}-propan-1-one;

4-Methyl-3-[methyl-(7H-pyrrolo[2,3-d]pyrimidin-4-yl)-amino]piperidine-1-carboxylic acid dimethylamide;

({4-Methyl-3-[methyl-(7H-pyrrolo[2,3-d]pyrimidin-4-yl)-amino]-piperidine-1-carbonyl}-amino)-acetic acid ethyl ester;

3-{4-Methyl-3-[methyl-(7H-pyrrolo[2,3-d]pyrimidin-4-yl)-amino]-piperidin-1-yl}-3-oxo-propionitrile;

3,3,3-Trifluoro-1-{4-methyl-3-[methyl-(5-methyl-7H-pyrrolo[2,3-d]pyrimidin-4-yl)-amino]-piperidin-1-yl}-propan-1-one;

1-{4-Methyl-3-[methyl-(7H-pyrrolo[2,3-d]pyrimidin-4-yl)-amino]-piperidin-1-yl}-but-3-yl-1-one;

1-{3-[(5-Chloro-7H-pyrrolo[2,3-d]pyrimidin-4-yl)-methyl-amino]-4-methyl-piperidin-1-yl}-propan-1-one;

1-{3-[(5-Fluoro-7H-pyrrolo[2,3-d]pyrimidin-4-yl)methyl-amino]-4-methyl-piperidin-1-yl}-propan-1-one;

N-cyano-4-methyl-3-[methyl-(7H-pyrrolo[2,3-d]pyrimidin-4-yl)-amino]-N'-propyl-piperidine-1-carboxamidine; and N-cyano-4,N',N'-Trimethyl-3-[methyl-(7H-pyrrolo[2,3-d]pyrimidin-4-amino]-piperidine-1-carboxamidine.

The present invention also relates to a pharmaceutical composition for (a) treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases or (b) the inhibition of protein kinases or Janus Kinase 3 (JAK3) in a mammal, including a human, comprising an amount of a compound of formula I or a pharmaceutically acceptable salt thereof, effective in such disorders or conditions and a pharmaceutically acceptable carrier.

The present invention also relates to a method for the inhibition of protein tyrosine kinases or Janus Kinase 3 (JAK3) in a mammal, including a human, comprising administering to said mammal an effective amount of a compound of formula I or a pharmaceutically acceptable salt thereof.

The present invention also relates to a method for treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases in a mammal, including a human, comprising administering to said mammal an amount of a compound of formula I or a pharmaceutically acceptable salt thereof, effective in treating such a condition.

DETAILED DESCRIPTION OF THE INVENTION

The following reaction Schemes illustrate the preparation of the compounds of the present invention. Unless otherwise indicated $R^2$, $R^3$, $R^4$ and $R^5$ in the reaction Schemes and the discussion that follow are defined as above.

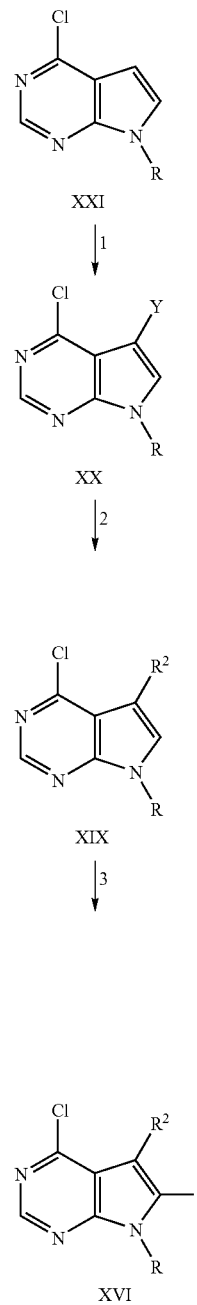

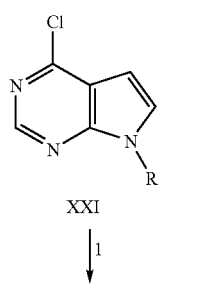

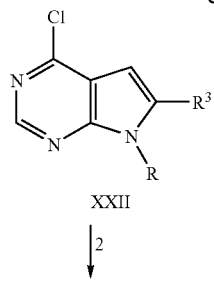
XXII
↓ 2
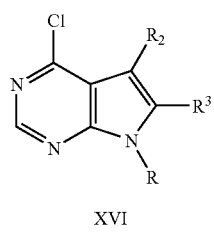
XVI
SCHEME 1
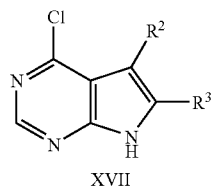
XVII
↓ 1
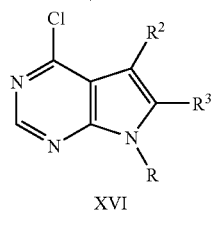
XVI
↓ 2
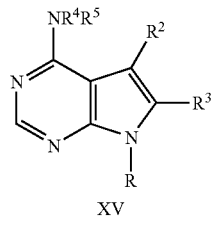
XV
↓ 3
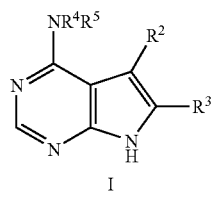
I
SCHEME 2
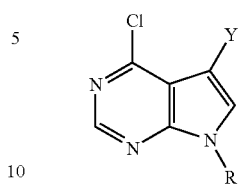
XX
↓ 1
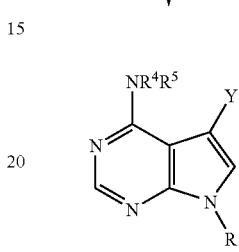
XXIV
↓ 2
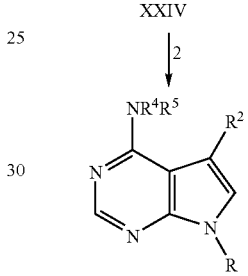
XXIII
↓ 3
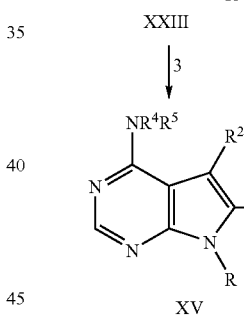
XV
SCHEME 3
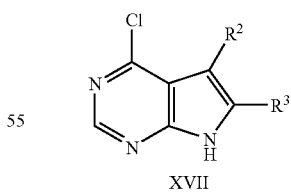
XVII
↓ 1
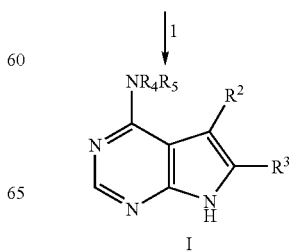
I In reaction 1 of Preparation A, the 4-chloropyrrolo[2,3-d]pyrimidine compound of formula XXI, wherein R is hydrogen or a protecting group such as benzenesulfonyl or benzyl, is converted to the 4-chloro-5-halopyrrolo[2,3-d]pyrimidine compound of formula XX, wherein Y is chloro, bromo or iodo, by reacting XXI with N-chlorosuccinimide, N-bromosuccinimide or N-iodosuccinimide. The reaction mixture is heated to reflux, in chloroform, for a time period between about 1 hour to about 3 hours, preferably about 1 hour. Alternatively, in reaction 1 of Preparation A, the 4-chloropyrrolo[2,3-d]pyrimidine of formula XXI, wherein R is hydrogen, is converted to the corresponding 4-chloro-5-nitropyrrolo[2,3-d]pyrimidine of formula XX, wherein Y is nitro, by reacting XXI with nitric acid in sulfuric acid at a temperature between about −10° C. to about 10° C., preferably about 0° C., for a time period between about 5 minutes to about 15 minutes, preferably about 10 minutes. The compound of formula XXI, wherein Y is nitro, is converted to the corresponding 4-chloro-5-aminopyrrolo[2,3-d]pyrimidine of the formula XX, wherein Y is amino, by reacting XXI under a variety of conditions known to one skilled in the art such as palladium hydrogenolysis or tin(IV)chloride and hydrochloric acid.

In reaction 2 of Preparation A, the 4-chloro-5-halopyrrolo[2,3-d]pyrimidine compound of formula XX, wherein R is hydrogen, is converted to the corresponding compound of formula XIX, wherein $R^2$ is ($C_1$-$C_6$)alkyl or benzyl, by treating XX with N-butyllithium, at a temperature of about −78° C., and reacting the dianion intermediate so formed with an alkylhalide or benzylhalide at a temperature between about −78° C. to room temperature, preferably room temperature. Alternatively, the dianion so formed is reacted with molecular oxygen to form the corresponding 4-chloro-5-hydroxypyrrolo[2,3-d]pyrimidine compound of formula XIX, wherein $R^2$ is hydroxy. The compound of formula XX, wherein Y is bromine or iodine and R is benzenesulfonate, is converted to the compound of formula XIX, wherein $R^2$ is ($C_6$-$C_{12}$)aryl or vinyl, by treating XX with N-butyllithium, at a temperature of about −78° C., followed by the addition of zinc chloride, at a temperature of about −78° C. The corresponding organo zinc intermediate so formed is then reacted with aryliodide or vinyl iodide in the presence of a catalytic quantity of palladium. The reaction mixture is stirred at a temperature between about 50° C. to about 80° C., preferably about 70° C., for a time period between about 1 hour to about 3 hours, preferably about 1 hour.

In reaction 3 of Preparation A, the compound of formula XIX is converted to the corresponding compound of formula XVI by treating XIX with N-butyllithium, lithium diisopropylamine or sodium hydride, at a temperature of about −78° C., in the presence of a polar aprotic solvent, such as tetrahydrofuran. The anionic intermediate so formed is further reacted with (a) alkylhalide or benzylhalide, at a temperature between about −78° C. to room temperature, preferably −78° C., when $R^3$ is alkyl or benzyl; (b) an aldehyde or ketone, at a temperature between about −78° C. to room temperature, preferably −78° C., when $R^3$ is alkoxy; and (c) zinc chloride, at a temperature between about −78° C. to room temperature, preferably −78° C., and the corresponding organozinc intermediate so formed is then reacted with aryliodide or vinyl iodide in the presence of a catalytic quantity of palladium. The resulting reaction mixture is stirred at a temperature between about 50° C. to about 80° C., preferably about 70° C., for a time period between about 1 hour to about 3 hours, preferably about 1 hour. Alternatively, the anion so formed is reacted with molecular oxygen to form the corresponding 4-chloro-6-hydroxypyrrolo[2,3-d]pyrimidine compound of formula XVI, wherein $R^3$ is hydroxy.

In reaction 1 of Preparation B, the 4-chloropyrrolo[2,3-d]pyrimidine compound of formula XXI is converted to the corresponding compound of formula XXII, according to the procedure described above in reaction 3 of Preparation A.

In reaction 2 of Preparation B, the compound of formula XXII is converted to the corresponding compound of formula XVI, according to the procedures described above in reactions 1 and 2 of Preparation A.

In reaction 1 of Scheme 1, the 4-chloropyrrolo[2,3-d]pyrimidine compound of formula XVII is converted to the corresponding compound of formula XVI, wherein R is benzenesulfonyl or benzyl, by treating XVII with benzenesulfonyl chloride, benzylchloride or benzylbromide in the presence of a base, such as sodium hydride or potassium carbonate, and a polar aprotic solvent, such as dimethylformamide or tetrahydrofuran. The reaction mixture is stirred at a temperature between about 0° C. to about 70° C., preferably about 30° C., for a time period between about 1 hour to about 3 hours, preferably about 2 hours.

In reaction 2 of Scheme 1, the 4-chloropyrrolo[2,3-d]pyrimidine compound of formula XVI is converted to the corresponding 4-aminopyrrolo[2,3-d]pyrimidine compound of formula XV by coupling XVI with an amine of the formula $HNR^4R^5$. The reaction is carried out in an alcohol solvent, such as tert-butanol, methanol or ethanol, or other high boiling organic solvents, such as dimethylformamide, triethylamine, 1,4-dioxane or 1,2-dichloroethane, at a temperature between about 60° C. to about 120° C., preferably about 80° C. Typical reaction times are between about 2 hours to about 48 hours, preferably about 16 hours. When $R^5$ is a nitrogen containing heterocycloalkyl group, each nitrogen must be protected by a protecting group, such a benzyl. Removal of the $R^5$ protecting group is carried out under conditions appropriate for that particular protecting group in use which will not affect the R protecting group on the pyrrolo[2,3-d]pyrimidine ring. Removal of the $R^5$ protecting group, when benzyl, is carried out in an alcohol solvent, such as ethanol, in the present of hydrogen and a catalyst, such as palladium hydroxide on carbon. The $R^5$ nitrogen containing hetrocycloalkyl group so formed may be further reacted with a variety of different electrophiles of formula II. For urea formation, electrophiles of formula it such as isocyanates, carbamates and carbamoyl chlorides are reacted with the $R^5$ nitrogen of the heteroalkyl group in a solvent, such as acetonitrile or dimethylformamide, in the presence of a base, such as sodium or potassium carbonate, at a temperature between about 20° C. to about 100° C. for a time period between about 24 hours to about 72 hours. For amide and sulfonamide formation, electrophiles of formula II, such as acylchlorides and sulfonyl chlorides, are reacted with the $R^5$ nitrogen of the heteroalkyl group in a solvent such as methylene chloride in the presence of a base such as pyridine at ambient temperatures for a time period between about 12 hours to about 24 hours. Amide formation may also be carried out by reacting a carboxylic acid with the heteroalkyl group in the presence of a carbodiimide such as 1-(3-dimethylaminopropyl)-3-ethylcarbodiimide in a solvent such as methylene chloride at ambient temperatures for 12-24 hours. For alkyl formation, electrophiles of formula II, such as α,β-unsaturated amides, acids, nitrites, esters, and α-halo amides, are reacted with the $R^5$ nitrogen of the heteroalkyl group in a solvent such as methanol at ambient temperatures for a time period between about 12 hours to about 18 hours. Alkyl formation may also be carried out by reacting aldehydes with the heteroalkyl group in the presence of a reducing agent, such as sodium cyanoborohydride, in a solvent, such as methanol, at ambient temperature for a time period between about 12 hours to about 18 hours.

In reaction 3 of Scheme 1, removal of the protecting group from the compound of formula XV, wherein R is benzenesulfonyl, to give the corresponding compound of formula I, is carried out by treating XV with an alkali base, such as sodium hydroxide or potassium hydroxide, in an alcohol solvent, such as methanol or ethanol, or mixed solvents, such as alcohol/tetrahydrofuran or alcohol/water. The reaction is carried out at room temperature for a time period between about 15 minutes to about 1 hour, preferably 30 minutes. Removal of the protecting group from the compound of formula XV, wherein R is benzyl, is conducted by treating XV with sodium in ammonia at a temperature of about −78° C. for a time period between about 15 minutes to about 1 hour.

In reaction 1 of Scheme 2, the 4-chloropyrrolo[2,3-d]pyrimidine compound of formula XX is converted to the corresponding 4-aminopyrrolo[2,3-d]pyrimidine compound of formula XXIV, according to the procedure described above in reaction 2 of Scheme 1.

In reaction 2 of Scheme 2, the 4-amino-5-halopyrrolo[2,3-d]pyrimidine compound of formula XXIV, wherein R is benzenesulfonate and Z is bromine or iodine, is converted to the corresponding compound of formula XXIII by reacting XXIV with (a) arylboronic acid, when $R^2$ is aryl, in an aprotic solvent, such tetrahydrofuran or dioxane, in the presence of a catalytic quantity of palladium (0) at a temperature between about 50° C. to about 100° C., preferably about 70° C., for a time period between about 2 hours to about 48 hours, preferably about 12 hours; (b) alkynes, when $R^2$ is alkynyl, in the presence of a catalytic quantity of copper (I) iodide and palladium (0), and a polar solvent, such as dimethylformamide, at room temperature, for a time period between about 1 hour to about 5 hours, preferably about 3 hours; and (c) alkenes or styrenes, when $R^2$ is vinyl or styrenyl, in the presence of a catalytic quantity of palladium in dimethylformamide, dioxane or tetrahydrofuran, at a temperature between about 80° C. to about 100° C., preferably about 100° C., for a time period between about 2 hours to about 48 hours, preferably about 48 hours.

In reaction 3 of Scheme 2, the compound of formula XXIII is converted to the corresponding compound of formula XV, according to the procedure described above in reaction 3 of Preparation A.

In reaction 1 of Scheme 3, the compound of formula XVII is converted to the corresponding compound of formula I, according to the procedure described above in reaction 2 of Scheme 1.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form nontoxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use. The active compounds of the invention may also be formulated in rectal-compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., asthma) in the average adult human are preferably arranged so that each metered dose or "puff" of aerosol contains 20 µg to 1000 µg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

A compound of formula (I) administered in a pharmaceutically acceptable form either alone or in combination with one or more, additional agents which modulate a mammalian immune system or with antiinflammatory agents, agents which may include but are not limited to cyclosporin A (e.g. Sandimmune® or Neoral®), rapamycin, FK-506 (tacrolimus), leflunomide, deoxyspergualin, mycophenolate (e.g. Cellcept®, azathioprine (e.g. Imuran®), daclizumab (e.g. Zenapax®), OKT3 (e.g. Orthocolone®), AtGam, aspirin, acctaminophen, ibuprofen, naproxen, piroxicam, and anti-inflammatory steroids (e.g. prednisolone or dexamethasone); and such agents may be administered as part of the same or separate, dosage forms, via the same or different routes of administration, and on the same or different administration schedules according to standard pharmaceutical practice.

FK506 (Tacrolimus) is given orally at 0.10-0.15 mg/kg body weight, every 12 hours, within first 48 hours postoperative. Does is monitored by serum Tacrolimus trough levels.

Cyclosporin A (Sandimmune oral or intravenous formulation, or Neoral®, oral solution or capsules) is given orally at 5 mg/kg body weight, every 12 hours within 48 hours postoperative. Dose is monitored by blood Cyclosporin A trough levels.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The ability of the compounds of formula I or their pharmaceutically acceptable salts to inhibit Janus Kinase 3 and, consequently, demonstrate their effectiveness for treating disorders or conditions characterized by Janus Kinase 3 is shown by the following in vitro assay tests.

Biological Assay

JAK3 (JH1:GST) Enzymatic Assay

The JAK3 kinase assay utilizes a protein expressed in baculovirus-infected SF9 cells (a fusion protein of GST and the catalytic domain of human JAK3) purified by affinity chromatography on glutathione-Sepaharose. The substrate for the reaction is poly-Glutamic acid-Tyrosine (PGT (4:1), Sigma catalog # P0275), coated onto Nunc Maxi Sorp plates at 100 µg/ml overnight at 37° C. The morning after coating, the plates are washed three times and JAK3 is added to the wells containing 100 µl of kinase buffer (50 mM HEPES, pH 7.3, 125 mM NaCl, 24 mM $MgCl_2$)+0.2 uM ATP+1 mM Na orthovanaidate.) The reaction proceeds for 30 minutes at room temperature and the plates is washed three more times. The level of phosphorylated tyrosine in a given well is quantitated by standard ELISA assay utilizing an anti-phosphotyrosine antibody (ICN PY20, cat. #69-151-1).

Inhibition of Human IL-2 Dependent T-Cell Blast Proliferation

This screen measures the inhibitory effect of compounds on IL-2 dependent T-Cell blast proliferation in vitro. Since signaling through the IL-2 receptor requires JAK-3, cell active inhibitors of JAK-3 should, inhibit IL-2 dependent T-Cell blast proliferation.

The cells for this assay are isolated from fresh human blood. After separation of the mononuclear cells using Accuspin System-Histopaque-1077 (Sigma # A7054), primary human T-Cells are isolated by negative selection using Lympho-Kwik T (One Lambda, Inc., Cat # LK-50T). T-Cells are cultured at $1\text{-}2\times10^6$/ml in Media (RPMI+10% heat-inactivated fetal calf serum (Hyclone Cat # A-1111-L)+1% Penicillin/Streptomycin (Gibco)) and induce to proliferate by the addition of 10 ug/ml PHA (Murex Diagnostics, Cat # HA 16). After 3 days at 37° C. in 5% $CO_2$, cells are washed 3 times in Media, resuspended to a density of $1\text{-}2\times10^6$ cells/ml in Media plus 100 Units/ml of human recombinant IL-2 (R&D Systems, Cat # 202-IL). After 1 week the cells are IL-2 dependent and can be maintained for up to 3 weeks by feeding twice weekly with equal volumes of Media+100 Units/ml of IL-2.

To assay for a test compounds ability to inhibit IL-2 dependent T-Cell; proliferation, IL-2 dependent cells are washed 3 times, resuspended in media and then plated (50,000 cells/well/0.1 ml) in a Flat-bottom 96-well microtiter plate (Falcon # 353075). From a 10 mM stock of test compound in DMSO, serial 2-fold dilutions of compound are added in triplicate wells starting at 10 uM. After one hour, 10 Units/ml of IL-2 is added to each test well. Plates are then incubated at 37° C., 5% $CO_2$ for 72 hours. Plates are then pulsed with $^3$H-thymidine (0.5 uCi/well) (NEN Cat # NET-027A), and incubated an additional 18 hours. Culture plates are then harvested with a 96-well plate harvester and the amount of $^3$H-thymidine incorporated into proliferating cells is determined by counting on a Packard Top Count scintillation counter. Data is analyzed by plotting the % inhibition of proliferation verses the concentration of test compound. An IC$_{50}$ value (uM) is determined from this plot.

The following Examples illustrate the preparation of the compounds of the present invention but it is not limited to the details thereof. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Low Resolution Mass Spectra (LRMS) were recorded on either a Hewlett Packard 5989®, utilizing chemical ionization (ammonium), or a Fisons (or Micro Mass). Atmospheric Pressure Chemical Ionization (APCI) platform which uses a 50/50 mixture of acetonitrile/water with 0.1% formic acid as the ionizing agent. Room or ambient temperature refers to 20-25° C.

EXAMPLE 1

1-{4-methyl-3-[methyl-7H-pyrrolo[2,3-d]pyrimidin-4-yl)-amino]-piperidin-1-yl}-ethanone Method A (1-Benzyl-4-methyl-piperidin-3-yl)-methyl-amine To a stirred solution of 1-benzyl-4-methyl-piperidin-3-one (2.3 grams, 11.5 mmol), prepared by the methods of Iorio, M. A. and Damia, G., Tetrahedron, 26, 5519 (1970) and Grieco et al., Journal of the American Chemical Society, 107, 1768 (1985), (modified using 5% methanol as a cosolvent), both references are incorporated by reference in their entirety, dissolved in 23 mL of 2 M methylamine in tetrahydrofuran was added 1.4 mL (23 mmol) of acetic acid and the resulting mixture stirred in a sealed tube for 16 hours at room temperature. Triacetoxy sodium borohydride (4.9 grams, 23 mmol) was added and the new mixture stirred at room temperature in a sealed tube for 24 h, at which time, the reaction was quenched upon addition of 1 N sodium hydroxide (50 mL). The reaction mixture was then extracted 3×80 mL with ether, the combined ether layers dried over sodium sulfate (Na$_2$SO$_4$) and concentrated to dryness in vacuo affording 1.7 grams (69%) of the title compound as a white solid. LRMS: 219.1 (M+1).

Method B (1-Benzyl-4-methyl-piperidin-3-yl)-methyl-(7H-pyrrolo[2,3-d]pyrimidin-4-yl)-amine A solution of 4-chloropyrrolo[2,3-d]pyrimidine (2.4 grams, 15.9 mmol), prepared by the method of Davoll, J. Am. Chem. Soc., 82, 131 (1960), which is incorporated by reference in its entirety, and the product from Method A (1.7 grams, 7.95 mmol) dissolved in 2 equivalents of triethylamine was heated in a sealed tube at 100° C. for 3 days. Following cooling to room temperature and concentration under reduced pressure, the residue was purified by flash chromatography (silica; 3% methanol in dichloromethane) affording 1.3 grams (50%) of the title compound as a colorless oil. LRMS: 336.1 (M+1).

Method C

Methyl-(4-methyl-piperidin-3-yl)-(7H-pyrrolo[2,3-d]pyrimidin-4-yl)-amine

To the product from Method B (0.7 grams, 2.19 mmol) dissolved in 15 mL of ethanol was added 1.5 mL of 2 N hydrochloric acid and the reaction mixture degassed by nitrogen purge. To the reaction mixture was then added 0.5 grams of 20% palladium hydroxide on carbon (50% water) (Aldrich) and the resulting mixture shaken (Parr-Shaker) under a 50 psi atmosphere of hydrogen at room temperature for 2 days. The Celite filtered reaction mixture was concentrated to dryness in vacuo and the residue purified by flash chromatography (silica; 5% methanol in dichloromethane) affording 0.48 grams (90%) of the title compound. LRMS: 246.1 (M+1).

Method D

1-{4-Methyl-3-[methyl-(7H-pyrrolo[2,3-d]pyrimidin-4-yl)-amino]-piperidin-1-yl}-ethanone To a stirred solution of the product from Method C (0.03 grams, 0.114 mmol) dissolved in 5 mL of 10:1 dichloromethane/pyridine was added (0.018 grams, 0.28 mmol) of acetylchloride and the resulting mixture stirred at room temperature for 18 hours. The reaction mixture was then partitioned between dichloromethane and saturated sodium bicarbonate (NaHCO$_3$). The organic layer was washed again with saturated NaHCO$_3$, dried over sodium sulfate and concentrated to dryness in vacuo. The residue was purified by preparative thin layer chromatography (PTLC) (silica; 4% methanol in dichloromethane) affording 0.005 mg (15%) of the title compound as a colorless oil. LRMS: 288.1 (M+1).

The title compounds for examples 2-26 were prepared by a method analogous to that described in Example 1.

EXAMPLE 2

[1-(2-Amino-ethanesulfonyl)-4-methyl-piperidin-3-yl]-methyl-(7H-pyrrolo[2,3-d]pyrimidin-4-yl)-amine

[1-(2-Amino-ethanesulfonyl)-4-methyl-piperidin-3-yl]-methyl-amine. LRMS: 353.

EXAMPLE 3

(1-Ethanesulfonyl-4-methyl-piperidin-3-yl)-methyl-(7H-pyrrolo[2,3-d]pyrimidin-4-yl)-amine (1-Ethanesulfonyl-4-methyl-piperidin-3-yl)-methyl-amine. LRMS: 338.

EXAMPLE 4

[1-Butane-1-sulfonyl)-4-methyl-piperidin-3-yl]-methyl-(7H-pyrrolo[2,3-d]pyrimidin-4-yl)-amine

[1-(Butane-1-sulfonyl)-4-methyl-piperidin-3-yl]-methyl-amine. LRMS: 366.

EXAMPLE 5

4-Methyl-3-[methyl-(7H-pyrrolo[2,3-d]pyrimidin-4-yl)-amino]-piperidine-1-carboxylic acid isobutyl ester 4-Methyl-3-methylamino-piperidine-1-carboxylic acid isobutyl ester. LRMS: 346.

EXAMPLE 6

N-(2-{4-Methyl-3-[methyl-(7H-pyrrolo[2,3-d]pyrimidin-4-yl)-amino]-piperidine-1-sulfonyl}-ethyl)-propionamide N-[2-(4-Methyl-3-methylamino-piperidine-1-sulfonyl) ethyl]-propionamide. LRMS: 409.

EXAMPLE 7

(2-{4-methyl-3-[methyl-(7H-pyrrolo[2,3-d]pyrimidin-4-yl)-amino]-piperidine-1-sulfonyl}-ethyl)-carbamic acid methyl ester

[2-(4-Methyl-3-methylamino-piperidine-1-sulfonyl)-ethyl]-carbamic acid methyl ester. LRMS: 411.

EXAMPLE 8

N-(2-{4-Methyl-3-[methyl-(7H-pyrrolo[2,3-d]pyrimidin-4-yl)-amino]-piperidine-1-sulfonyl}-ethyl)-isobutyramide N-[2-(4-Methyl-3-methylamino-piperidine-1-sulfonyl)-ethyl-isobutyramide. LRMS: 423.

EXAMPLE 9

(1-Methanesulfonyl-piperidin-3-yl)-methyl-(7H-pyrrolo[2,3-d]pyrimidin-4-yl)-amine
(1-Methanesulfonyl-piperidin-3-yl)methyl-amine. LRMS: 310.

EXAMPLE 10

(1-Ethanesulfonyl-piperidin-3-yl)-methyl-(7H-pyrrolo[2,3-d]pyrimidin-4-yl)-amine (1-Ethanesulfonyl-piperidin-3-yl)-methyl-amine. LRMS: 324.

EXAMPLE 11

Methyl-[1-(Propane-1-sulfonyl)-piperidin-3-yl]-(7H-pyrrolo[2,3-d]pyrimidin-4-yl)-amine (1-Propylsulfonyl-piperidin-3-yl)-methyl-amine. LRMS: 338.

EXAMPLE 12

[1-(Butane-1-sulfonyl)-piperidin-3-yl]-methyl-(7H-pyrrolo[2,3-d]pyrimidin-4-yl)-amine (1-Butylsulfonyl-piperidin-3-yl)-methyl-amine. LRMS: 352.

EXAMPLE 13

2,2-Dimethyl-N-(2-{4-methyl-3-[methyl-(7H-pyrrolo[2,3-d]pyrimidin-4-yl)-amino]-piperidine-1-sulfonyl}-ethyl)-propionamide 2,2-Dimethyl-N-[2-(4-methyl-3-methylamino-piperidine-1-sulfonyl)-ethyl]-propionamide. LRMS: 437.

EXAMPLE 14

3-{4-Methyl-3-[methyl-(7H-pyrrolo[2,3-d]pyrimidin-4-yl)amino]-piperidin-1-yl}-3-oxo-propionitrile 3-(4-Methyl-3-methylamino-piperidin-1-yl)-3-oxo-propionitrile. LRMS: 313.

EXAMPLE 15

(3-{4-Methyl-3-[methyl-(7H-pyrrolo[2,3-d]pyrimidin-4-yl)-amino]-piperidin-1-yl}-3-oxo-propyl)-carbamic acid tert-butyl ester

[3-(4-Methyl-3-methylamino-piperidin-1-yl)-3-oxo-propyl]-carbamic add tert-butyl ester. LRMS: 417.

EXAMPLE 16

Methyl-[4-methyl-1-(propane-1-sulfonyl)-piperidin-3-yl]-(7H-pyrrolo[2,3-d]pyrimidin-4-yl)-amine Methyl-[4-methyl-1-(propane-1-sulfonyl)-piperidin-3-yl]-amine. LRMS: 352.

EXAMPLE 17

3-Amino-1-{4-methyl-3-[methyl-(7H pyrrolo[2,3-d]pyrimidin-4-yl)-amino]-piperidin-1-yl}-propan-1-one 3-Amino-1-(4-methyl-3-methylamino-piperidin-1-yl)-propan-1-one. LRMS: 317.

EXAMPLE 18

2-Methoxy-1-{4-methyl-3-[methyl-(7H-pyrrolo[2,3-d]pyrimidin-4-yl)-amino]-piperidin-1-yl}-ethanone 2-Methoxy-1-(4-methyl-3-methylamino-piperidin-1-yl)-ethanone. LRMS: 318.

EXAMPLE 19

2-Dimethylamino-1-{4-methyl-3-[methyl-(7H-pyrrolo[2,3-d]pyrimidin-4-yl)-amino]-piperidin-1-yl}-ethanone 2-Dimethylamino-1-(4-methyl-3-methylamino-piperidin-1-yl)-ethanone. LRMS: 331.

EXAMPLE 20

(3-{4-Methyl-3-[methyl-(7H-pyrrolo[2,3-d]pyrimidin-4-yl)-amino]-piperidin-1-yl}-3-oxo-propyl)-carbamic acid tert-butyl ester

[3-(4-Methyl-3-methylamino-piperidin-1-yl)-3-oxo-propyl]-carbamic acid tert-butyl ester. LRMS: 417.

EXAMPLE 21

3,3,3-Trifluoro-1-{4-methyl-3-[methyl-(7H-pyrrolo[2,3-d]pyrimidin-4-yl)-amino]-piperidin-1-yl}-propan-1-one 3,3,3-Trifluoro-1-(4-methyl-3-methylamino-piperidin-1-yl)-propan-1-one.

EXAMPLE 22

N-(2-{4-Methyl-3-[methyl-(7H-pyrrolo[2,3-d]pyrimidin-4-yl)-amino]-piperidin-1-yl}-2-oxo-ethyl)-acetamide N-[2-(4-Methyl-3-methylamino-piperidin-1-yl)-2-oxo-ethyl]-acetamide. LRMS: 345.

EXAMPLE 23

3-Ethoxy-1-{4-methyl-3-[methyl-(7H-pyrrolo[2,3-d]pyrimidin-4-yl)-amino]-piperidin-1-yl}-propan-1-one 3-Ethoxy-1-(4-methyl-3-methylamino-piperidin-1-yl)-propan-1-one. LRMS: 346.

EXAMPLE 24

4-Methyl-3-[methyl-(7H-pyrrolo[2,3-d]pyrimidin-4-yl)-amino]-piperidine-1-carboxylic acid methylamide 4-Methyl-3-methylamino-piperidine-1-carboxylic acid methylamide. LRMS: 303.

EXAMPLE 25

4-Methyl-3-[methyl-(7H-pyrrolo[2,3-d]pyrimidin-4-yl)-amino]-piperidine-1-carboxylic acid diethylamide 4-Methyl-3-methylamino-piperidine-1-carboxylic acid diethylamide. LRMS: 345.

EXAMPLE 26

Methyl-[4-methyl-1-(2-methylamino-ethanesulfonyl)-piperidin-3-yl]-(7H-pyrrolo[2,3-d]pyrimidin-4-yl)-amine Methyl-[4-methyl-1-(2-methylamino-ethanesulfonyl)-piperidin-3-yl]-amine. LRMS: 367.

The invention claimed is:

1. A compound of the Formula I;

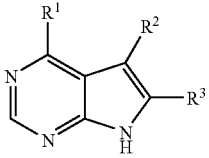

or a pharmaceutically acceptable salt thereof; wherein
$R^1$ is a group of the formula

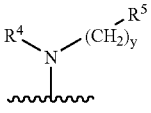

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$ amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $(C_1-C_6)$alkyl-S(O)$_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula

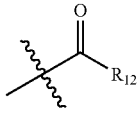

wherein $R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$ amino, amino$(C_1-C_6)$alkyl, $(C_1-C_6)$ alkoxy-CO—NH, (C$_1$-C$_6$)alkylamino-CO—, (C$_2$-C$_6$)alkenyl, (C$_2$-C$_6$)alkynyl, (C$_1$-C$_6$)alkylamino, hydroxy(C$_1$-C$_6$)alkyl, (C$_1$-C$_6$)alkoxy(C$_1$-C$_6$)alkyl, (C$_1$-C$_6$)acyloxy(C$_1$-C$_6$)alkyl, nitro, cyano(C$_1$-C$_6$)alkyl, halo(C$_1$-C$_6$)alkyl, nitro(C$_1$-C$_6$)alkyl, trifluoromethyl, trifluoromethyl(C$_1$-C$_6$)alkyl, (C$_1$-C$_6$)acylamino, (C$_1$-C$_6$)acylamino(C$_1$-C$_6$)alkyl, (C$_1$-C$_6$)alkoxy(C$_1$-C$_6$)acylamino, amino(C$_1$-C$_6$)acyl, amino(C$_1$-C$_6$)acyl(C$_1$-C$_6$)alkyl, (C$_1$-C$_6$)alkylamino(C$_1$-C$_6$)acyl, ((C$_1$-C$_6$)alkyl)$_2$amino(C$_1$-C$_6$)acyl, R$^{15}$R$^{16}$N—CO—O—, R$^{15}$R$^{16}$N—CO—(C$_1$-C$_6$)alkyl, R$^{15}$C(O)NH, R$^{15}$OC(O)NH, R$^{15}$NHC(O)NH, (C$_1$-C$_6$)alkyl-S(O)$_m$, (C$_1$-C$_6$)alkyl-S(O)$_m$(C$_1$-C$_6$)alkyl, R$^{15}$R$^{16}$NS(O)$_m$, R$^{15}$R$^{16}$NS(O)$_m$(C$_1$-C$_6$)alkyl, R$^{15}$S(O)$_m$R$^{16}$N, R$^{15}$S(O)$_m$R$^{16}$N(C$_1$-C$_6$)alkyl wherein m is 0, 1 or 2 and R$^{15}$ and R$^{16}$ are each independently selected from hydrogen or (C$_1$-C$_6$)alkyl;

R$^2$ and R$^3$ are each hydrogen.

2. A compound of the Formula I;

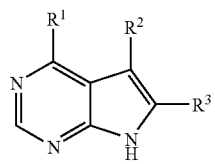

or a pharmaceutically acceptable salt thereof; wherein
R$^1$ is a group of the formula

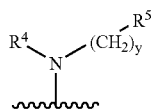

wherein y is 0, 1 or 2;
R$^4$ is selected from the group consisting of hydrogen; (C$_1$-C$_6$)alkyl, (C$_1$-C$_6$)alkylsulfonyl, (C$_2$-C$_6$)alkenyl, (C$_2$-C$_6$)alkynyl wherein the alkyl, alkenyl and alkynyl groups are optionally substituted by deuterium, hydroxy, amino, trifluoromethyl, (C$_1$-C$_4$)alkoxy, (C$_1$-C$_6$)acyloxy, (C$_1$-C$_6$)alkylamino, ((C$_1$-C$_6$)alkyl)$_2$amino, cyano, nitro, (C$_2$-C$_6$)alkenyl, (C$_2$-C$_6$)alkynyl or (C$_1$-C$_6$)acylamino; or R$^4$ is (C$_3$-C$_{10}$)cycloalkyl wherein the cycloalkyl group is optionally substituted by deuterium, hydroxy, amino, trifluoromethyl, (C$_1$-C$_6$)acyloxy, (C$_1$-C$_6$)acylamino, (C$_1$-C$_6$)alkylamino, ((C$_1$-C$_6$)alkyl)$_2$amino, cyano, cyano(C$_1$-C$_6$)alkyl, trifluoromethyl(C$_1$-C$_6$)alkyl, nitro, nitro(C$_1$-C$_6$)alkyl or (C$_1$-C$_6$)acylamino;
R$^5$ is a piperidinyl substituted by one to five carboxy, cyano, amino, deuterium, hydroxy, (C$_1$-C$_6$)alkyl, (C$_1$-C$_6$)alkoxy, halo, (C$_1$-C$_6$)acyl, (C$_1$-C$_6$)alkylamino, amino(C$_1$-C$_6$)alkyl, (C$_1$-C$_6$)alkoxy-CO—NH, (C$_1$-C$_6$)alkylamino-CO—, (C$_2$-C$_6$)alkenyl, (C$_2$-C$_6$)alkynyl, (C$_1$-C$_6$)alkylamino, amino(C$_1$-C$_6$)alkyl, hydroxy(C$_1$-C$_6$)alkyl, (C$_1$-C$_6$)alkoxy(C$_1$-C$_6$)alkyl, (C$_1$-C$_6$)acyloxy(C$_1$-C$_6$)alkyl, nitro, cyano(C$_1$-C$_6$)alkyl, halo(C$_1$-C$_6$)alkyl, nitro(C$_1$-C$_6$)alkyl, trifluoromethyl, trifluoromethyl(C$_1$-C$_6$)alkyl, (C$_1$-C$_6$)acylamino, (C$_1$-C$_6$)acylamino(C$_1$-C$_6$)alkyl, (C$_1$-C$_6$)alkoxy(C$_1$-C$_6$)acylamino, amino(C$_1$-C$_6$)acyl, amino(C$_1$-C$_6$)acyl(C$_1$-C$_6$)alkyl, (C$_1$-C$_6$)alkylamino(C$_1$-C$_6$)acyl, ((C$_1$-C$_6$)alkyl)$_2$amino(C$_1$-C$_6$)acyl, R$^{15}$R$^{16}$N—CO—O—, R$^{15}$R$^{16}$N—CO—(C$_1$-C$_6$)alkyl, (C$_1$-C$_6$)alkyl-S(O)$_m$, R$^{15}$R$^{16}$NS(O)$_m$, R$^{15}$R$^{16}$NS(O)$_m$(C$_1$-C$_6$)alkyl, R$^{15}$S(O)$_m$R$^{16}$N, R$^{15}$S(O)$_m$R$^{16}$N(C$_1$-C$_6$)alkyl wherein m is 0, 1 or 2 and R$^{15}$ and R$^{16}$ are each independently selected from hydrogen or (C$_1$-C$_6$)alkyl; or a group of the formula

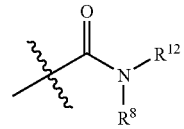

wherein R$^8$ is selected from the group consisting of hydrogen or (C$_1$-C$_6$)alkyl optionally substituted by deuterium, hydroxy, amino, trifluoromethyl, (C$_1$-C$_6$)acyloxy, (C$_1$-C$_6$)acylamino, (C$_1$-C$_6$)alkylamino, ((C$_1$-C$_6$)alkyl)$_2$amino, cyano, cyano(C$_1$-C$_6$)alkyl, trifluoromethyl(C$_1$-C$_6$)alkyl, nitro, nitro(C$_1$-C$_6$)alkyl or (C$_1$-C$_6$)acylamino;
R$^{12}$ is carboxy, cyano, amino, oxo, deuterium, hydroxy, trifluoromethyl, (C$_1$-C$_6$)alkyl, trifluoromethyl(C$_1$-C$_6$)alkyl, (C$_1$-C$_6$)alkoxy, halo, (C$_1$-C$_6$)acyl, (C$_1$-C$_6$)alkylamino, ((C$_1$-C$_6$)alkyl)$_2$amino, amino(C$_1$-C$_6$)alkyl, (C$_1$-C$_6$)alkoxy-CO—NH, (C$_1$-C$_6$)alkylamino-CO—, (C$_2$-C$_6$)alkenyl, (C$_2$-C$_6$)alkynyl, (C$_1$-C$_6$)alkylamino, hydroxy(C$_1$-C$_6$)alkyl, (C$_1$-C$_6$)alkoxy(C$_1$-C$_6$)alkyl, (C$_1$-C$_6$)acyloxy(C$_1$-C$_6$)alkyl, nitro, cyano(C$_1$-C$_6$)alkyl, halo(C$_1$-C$_6$)alkyl, nitro(C$_1$-C$_6$)alkyl, trifluoromethyl, trifluoromethyl(C$_1$-C$_6$)alkyl, (C$_1$-C$_6$)acylamino, (C$_1$-C$_6$)acylamino(C$_1$-C$_6$)alkyl, (C$_1$-C$_6$)alkoxy(C$_1$-C$_6$)acylamino, amino(C$_1$-C$_6$)acyl, amino(C$_1$-C$_6$)acyl(C$_1$-C$_6$)alkyl, (C$_1$-C$_6$)alkylamino(C$_1$-C$_6$)acyl, ((C$_1$-C$_6$)alkyl)$_2$amino(C$_1$-C$_6$)acyl, R$^{15}$R$^{16}$N—CO—O—, R$^{15}$R$^{16}$N—CO—(C$_1$-C$_6$)alkyl, R$^{15}$C(O)NH, R$^{15}$OC(O)NH, R$^{15}$NHC(O)NH, (C$_1$-C$_6$)alkyl-S(O)$_m$, (C$_1$-C$_6$)alkyl-S(O)$_m$—(C$_1$-C$_6$)alkyl, R$^{15}$R$^{16}$NS(O)$_m$, R$^{15}$R$^{16}$NS(O)$_m$(C$_1$-C$_6$)alkyl, R$^{15}$S(O)$_m$R$^{16}$N, R$^{15}$S(O)$_m$R$^{16}$N(C$_1$-C$_6$)alkyl wherein m is 0, 1 or 2 and R$^{15}$ and R$^{16}$ are each independently selected from hydrogen or (C$_1$-C$_6$)alkyl R$^2$ and R$^3$ are each hydrogen.

3. A compound of the Formula I;

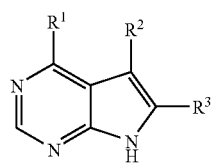

or a pharmaceutically acceptable salt thereof; wherein
R$^1$ is a group of the formula

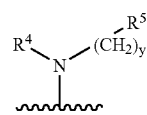

wherein y is 0, 1 br 2;
R$^4$ selected from the group consisting of hydrogen, (C$_1$-C$_6$)alkyl, (C$_1$-C$_6$)alkylsulfonyl, (C$_2$-C$_6$)alkenyl, (C$_2$-C$_6$)alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$ amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$ alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$ alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$ alkyl, $(C_1-C_6)$alkylamino$(C_1-C_6)$acyl, $((C_1-C_6)$alkyl$)_2$ amino$(C_1-C_6)$acyl, $R^{15}R^{16}N$—CO—O—, $R^{15}R^{16}N$—CO—$(C_1-C_6)$alkyl, $(C_1-C_6)$alkyl-$S(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula

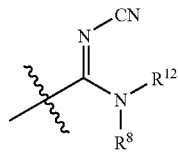

wherein $R^8$ is independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$ alkyl$)_2$ amino, cyano, cyano$(C_1-C_6)$alkyl, trifluoromethyl $(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$ alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_2-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$ alkyl, $(C_1-C_6)$alkylamino$(C_1-C_6)$acyl, $((C_1-C_6)$alkyl$)_2$ amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-$S(O)_m$, $(C_1-C_6)$alkyl-$S(O)_m$-$(C_1-C_6)$alkyl, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$ alkyl wherein m is 0, 1 or 2 and $R^{15}$ and $R^{16}$ are each independently selected from hydrogen or $(C_1-C_6)$alkyl; $R^2$ and $R^3$ are each hydrogen.

4. A compound of the Formula I;

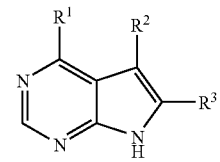

or a pharmaceutically acceptable salt thereof; wherein
$R^1$ is a group of the formula

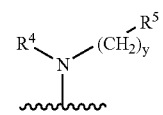

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkylamino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$ amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$ alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$ alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$ alkyl, $(C_1-C_6)$alkylamino$(C_1-C_6)$acyl, $((C_1-C_6)$alkyl$)_2$ amino$(C_1-C_6)$acyl, $R^{15}R^{16}N$—CO—O—, $R^{15}R^{16}N$—CO—$(C_1-C_6)$alkyl, $(C_1-C_6)$alkyl-$S(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula

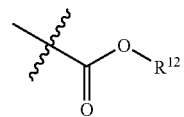

wherein $R^{12}$ is carboxy, cyano, amino, oxo, deuterium, hydroxy, trifluoromethyl, $(C_1-C_6)$alkyl, trifluoromethyl$(C_1-$ $C_6$)alkyl, ($C_1$-$C_6$)alkoxy, halo, ($C_1$-$C_6$)acyl, ($C_1$-$C_6$)alkylamino, (($C_1$-$C_6$)alkyl)$_2$ amino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}$N—CO—O—, $R^{15}R^{16}$N—CO—($C_1$-$C_6$)alkyl, $R^{15}$C(O)NH, $R^{15}$OC(O)NH, $R^{15}$NHC(O)NH, ($C_1$-$C_6$)alkyl-S(O)$_m$, ($C_1$-$C_6$)alkyl-S(O)$_m$-($C_1$-$C_6$)alkyl, $R^{15}R^{16}$NS(O)$_m$, $R^{15}R^{16}$NS(O)$_m$($C_1$-$C_6$)alkyl, $R^{15}$S(O)$_m$$R^{16}$N, $R^{15}$S(O)$_m$$R^{16}$N($C_1$-$C_6$)alkyl wherein m is 0, 1 or 2 and $R^{15}$ and $R^{16}$ are each independently selected from hydrogen or ($C_1$-$C_6$)alkyl;

$R^2$ and $R^3$ are each hydrogen.

5. A compound of the Formula I;

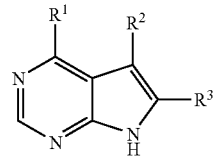

I or a pharmaceutically acceptable salt thereof; wherein
$R^1$ is a group of the formula

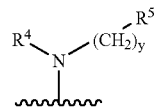

wherein y is 0, 1 or 2;
$R^4$ is selected from the group consisting of hydrogen, ($C_1$-$C_6$)alkyl, ($C_1$-$C_6$)alkylsulfonyl, ($C_2$-$C_6$)alkenyl, ($C_2$-$C_6$)alkynyl wherein the alkyl, alkenyl and alkynyl groups are optionally substituted by deuterium, hydroxy, amino, trifluoromethyl, ($C_1$-$C_4$)alkoxy, ($C_1$-$C_6$)acyloxy, ($C_1$-$C_6$)alkylamino, (($C_1$-$C_6$)alkyl)$_2$amino, cyano, nitro, ($C_2$-$C_6$)alkenyl, ($C_2$-$C_6$)alkynyl or ($C_1$-$C_6$)acylamino; or $R^4$ is ($C_3$-$C_{10}$)cycloalkyl wherein the cycloalkyl group is optionally substituted by deuterium, hydroxy, amino, trifluoromethyl, ($C_1$-$C_6$)acyloxy, ($C_1$-$C_6$)acylamino, ($C_1$-$C_6$)alkylamino, (($C_1$-$C_6$)alkyl)$_2$ amino, cyano, cyano($C_1$-$C_6$)alkyl, trifluoromethyl($C_1$-$C_6$)alkyl, nitro, nitro($C_1$-$C_6$)alkyl or ($C_1$-$C_6$)acylamino;
$R^5$ is a piperidinyl substituted by one to five carboxy, cyano, amino, deuterium, hydroxy, ($C_1$-$C_6$)alkyl, ($C_1$-$C_6$)alkoxy, halo, ($C_1$-$C_6$)acyl, ($C_1$-$C_6$)alkylamino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, amino($C_1$-$C_6$)alkyl, hydroxy($C_1$-$C_6$)alkyl, ($C_1$-$C_6$)alkoxy($C_1$-$C_6$)alkyl, ($C_1$-$C_6$)acyloxy ($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}$N—CO—O—, $R^{15}R^{16}$N—CO—($C_1$-$C_6$)alkyl, $R^{15}$C(O)NH, $R^{15}$OC(O)NH, $R^{15}$NHC(O)NH, ($C_1$-$C_6$)alkyl-S(O)$_m$, ($C_1$-$C_6$)alkyl-S(O)$_m$-($C_1$-$C_6$)alkyl, $R^{15}R^{16}$NS(O)$_m$, $R^{15}R^{16}$NS(O)$_m$($C_1$-$C_6$)alkyl, $R^{15}$S(O)$_m$$R^{16}$N, $R^{15}$S(O)$_m$$R^{16}$N($C_1$-$C_6$)alkyl wherein m is 0, 1 or 2 and $R^{15}$ and $R^{16}$ are each independently selected from hydrogen or ($C_1$-$C_6$)alkyl; or a group of the formula

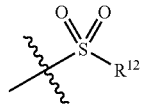

wherein $R^{12}$ is carboxy, cyano, amino, oxo, deuterium, hydroxy, trifluoromethyl, ($C_1$-$C_6$)alkyl, trifluoromethyl($C_1$-$C_6$)alkyl, ($C_1$-$C_6$)alkoxy, halo, ($C_1$-$C_6$)acyl, ($C_1$-$C_6$)alkylamino, (($C_1$-$C_6$)alkyl)$_2$ amino, amino($C_1$-$C_6$)alkyl, ($C_1$-$C_6$) alkoxy-CO—NH, ($C_1$-$C_6$)alkylamino-CO—, ($C_2$-$C_6$) alkenyl, ($C_2$-$C_6$)alkynyl, ($C_1$-$C_6$)alkylamino, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$) alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}$N—CO—O—, $R^{15}R^{16}$N—CO—($C_1$-$C_6$)alkyl, $R^{15}$C(O)NH, $R^{15}$OC(O)NH, $R^{15}$NHC(O)NH, ($C_1$-$C_6$)alkyl-S(O)$_m$, ($C_1$-$C_6$)alkyl-S(O)$_m$—($C_1$-$C_6$)alkyl, $R^{15}R^{16}$NS(O)$_m$, $R^{15}R^{16}$NS(O)$_m$($C_1$-$C_6$) alkyl, $R^{15}$S(O)$_m$$R^{16}$N, $R^{15}$S(O)$_m$$R^{16}$N($C_1$-$C_6$)alkyl wherein m is 0, 1 or 2 and $R^{15}$ and $R^{16}$ are each independently selected from hydrogen or ($C_1$-$C_6$)alkyl;

$R^2$ and $R^3$ are each hydrogen.

6. A compound of the Formula I;

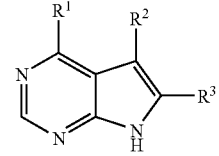

I or a pharmaceutically acceptable salt thereof; wherein
$R^1$ is a group of the formula

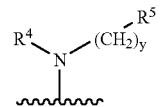

wherein y is 0, 1 or 2;
$R^4$ is selected from the group consisting of hydrogen, ($C_1$-$C_6$)alkyl, ($C_1$-$C_6$)alkylsulfonyl, ($C_2$-$C_6$)alkenyl, ($C_2$-$C_6$)alkynyl wherein the alkyl, alkenyl and alkynyl groups are, optionally substituted by deuterium, hydroxy, amino, trifluoromethyl, ($C_1$-$C_4$)alkoxy, ($C_1$-$C_6$)acyloxy, ($C_1$-$C_6$)alkylamino, (($C_1$-$C_6$)alkyl)$_2$amino, cyano, nitro, ($C_2$-$C_6$)alkenyl, ($C_2$-$C_6$)alkynyl or ($C_1$-$C_6$)acylamino; or $R^4$ is ($C_3$-$C_{10}$)cycloalkyl wherein the cycloalkyl group is optionally substituted by deute rium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$ alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $C_1-C_6$alkyl-$S(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula

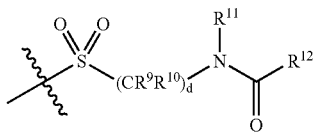

wherein d is 2;

$R^9$, $R^{10}$, and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-$S(O)_m$, $(C_1-C_6)$alkyl-$S(O)_m$-$(C_1-C_6)$alkyl, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each hydrogen.

7. A compound of the Formula I;

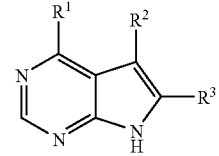

or a pharmaceutically acceptable salt thereof; wherein
$R^1$ is a group of the formula

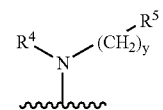

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$ alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $C_1-C_6$acyloxy $(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $(C_1-C_6)$alkyl-$S(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula

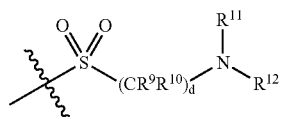

wherein d is 2;

$R^9$, $R^{10}$, and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-$ $C_6$)alkyl, trifluoromethyl($C_1$-$C_6$)alkyl, nitro, nitro($C_1$-$C_6$)alkyl or ($C_1$-$C_6$)acylamino;

$R^{12}$ is carboxy, cyano, amino, oxo, deuterium, hydroxy, trifluoromethyl, ($C_1$-$C_6$)alkyl, trifluoromethyl($C_1$-$C_6$)alkyl, ($C_1$-$C_6$)alkoxy, halo, ($C_1$-$C_6$)acyl, ($C_1$-$C_6$)alkylamino, (($C_1$-$C_6$)alkyl)$_2$amino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}N$—CO—O—, $R^{15}R^{16}N$—CO—($C_1$-$C_6$)alkyl, $R^{15}C(O)NH$, $R^{15}OC(O)NH$, $R^{15}NHC(O)NH$, ($C_1$-$C_6$)alkyl-S(O)$_m$, ($C_1$-$C_6$)alkyl-S(O)$_m$-($C_1$-$C_6$)alkyl, $R^{15}R^{16}NS(O)_m$, $R^{15}R^{16}NS(O)_m$($C_1$-$C_6$)alkyl, $R^{15}S(O)_m R^{16}N$, $R^{15}S(O)_m R^{16}N($C_1$-$C_6$)alkyl wherein m is 0, 1 or 2 and $R^{15}$ and $R^{16}$ are each independently selected from hydrogen or ($C_1$-$C_6$)alkyl;

$R^2$ and $R^3$ are each hydrogen.

8. A compound of the Formula I;

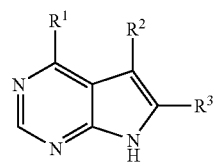

or a pharmaceutically acceptable salt thereof; wherein $R^1$ is a group of the formula

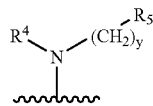

wherein y is 0, 1 or 2;

$R^4$ is selected from the group consisting of hydrogen, ($C_1$-$C_6$)alkyl, ($C_1$-$C_6$)alkylsulfonyl, ($C_2$-$C_6$)alkenyl, ($C_2$-$C_6$)alkynyl wherein the alkyl, alkenyl and alkynyl groups are optionally substituted by deuterium, hydroxy, amino, trifluoromethyl, ($C_1$-$C_4$)alkoxy, ($C_1$-$C_6$)acyloxy, ($C_1$-$C_6$)alkylamino, (($C_1$-$C_6$)alkyl)$_2$amino, cyano, nitro, ($C_2$-$C_6$)alkenyl, ($C_2$-$C_6$)alkynyl or ($C_1$-$C_6$)acylamino; or $R^4$ is ($C_3$-$C_{10}$)cycloalkyl wherein the cycloalkyl group is optionally substituted by deuterium, hydroxy, amino, trifluoromethyl, ($C_1$-$C_6$)acyloxy, ($C_1$-$C_6$)acylamino, ($C_1$-$C_6$)alkylamino, (($C_1$-$C_6$)alkyl)$_2$amino, cyano, cyano($C_1$-$C_6$)alkyl, trifluoromethyl($C_1$-$C_6$)alkyl, nitro, nitro($C_1$-$C_6$)alkyl or ($C_1$-$C_6$)acylamino;

$R^5$ is a piperidinyl substituted by one to five carboxy, cyano, amino, deuterium, hydroxy, ($C_1$-$C_6$)alkyl, ($C_1$-$C_6$)alkoxy, halo, ($C_1$-$C_6$)acyl, ($C_1$-$C_6$)alkylamino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, amino($C_1$-$C_6$)alkyl, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}N$—CO—O—, $R^{15}R^{16}N$—CO—($C_1$-$C_6$)alkyl, ($C_1$-$C_6$)alkyl-S(O)$_m$, $R^{15}R^{16}NS(O)_m$, $R^{15}R^{16}NS(O)_m$($C_1$-$C_6$)alkyl, $R^{15}S(O)_m R^{16}N$, $R^{15}S(O)_m R^{16}N($C_1$-$C_6$)alkyl wherein m is 0, 1 or 2 and $R^{15}$ and $R^{16}$ are each independently selected from hydrogen or ($C_1$-$C_6$)alkyl; or a group of the formula

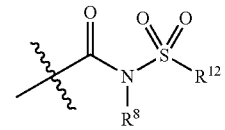

wherein $R^8$ is selected from the group consisting of hydrogen or ($C_1$-$C_6$)alkyl optionally substituted by deuterium, hydroxy, amino, trifluoromethyl, ($C_1$-$C_6$)acyloxy, ($C_1$-$C_6$)acylamino, ($C_1$-$C_6$)alkylamino, (($C_1$-$C_6$)alkyl)$_2$amino, cyano, cyano($C_1$-$C_6$)alkyl, trifluoromethyl($C_1$-$C_6$)alkyl, nitro, nitro($C_1$-$C_6$)alkyl or ($C_1$-$C_6$)acylamino;

$R^{12}$ is carboxy, cyano, amino, oxo, deuterium, hydroxy, trifluoromethyl, ($C_1$-$C_6$)alkyl, trifluoromethyl($C_1$-$C_6$)alkyl, ($C_1$-$C_6$)alkoxy, halo, ($C_1$-$C_6$)acyl, ($C_1$-$C_6$)alkylamino, (($C_1$-$C_6$)alkyl)$_2$amino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}N$—CO—O—, $R^{15}R^{16}N$—CO—($C_1$-$C_6$)alkyl, $R^{15}C(O)NH$, $R^{15}OC(O)NH$, $R^{15}NHC(O)NH$, ($C_1$-$C_6$)alkyl-S(O)$_m$, ($C_1$-$C_6$)alkyl-S(O)$_m$-($C_1$-$C_6$)alkyl, $R^{15}R^{16}NS(O)_m$, $R^{15}R^{16}NS(O)_m$($C_1$-$C_6$)alkyl, $R^{15}S(O)_m R^{16}N$, $R^{15}S(O)_m R^{16}N($C_1$-$C_6$)alkyl wherein m is 0, 1 or 2 and $R^{15}$ and $R^{16}$ are each independently selected from hydrogen or ($C_1$-$C_6$)alkyl;

$R^2$ and $R^3$ are each hydrogen.

9. A compound of the Formula I;

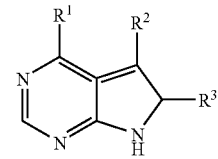

or a pharmaceutically acceptable salt thereof; wherein $R^1$ is a group of the formula

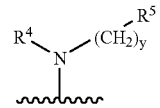

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_2-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$ amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}$N—CO—O—, $R^{15}R^{16}$N—CO—$(C_1-C_6)$alkyl, $(C_1-C_6)$alkyl-S(O)$_m$, $R^{15}R^{16}$NS(O)$_m$, $R^{15}R^{16}$NS(O)$_m(C_1-C_6)$alkyl, $R^{15}$S(O)$_m R^{16}$N, $R^{15}$S(O)$_m R^{16}$N$(C_1-C_6)$alkyl wherein m is 0, 1 or 2 and $R^{15}$ and $R^{16}$ are each independently selected from hydrogen or $(C_1-C_6)$alkyl; or a group of the formula

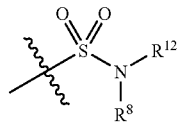

wherein $R^8$ is selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}$N—CO—O—, $R^{15}R^{16}$N—CO—$(C_1-C_6)$alkyl, $R^{15}$C(O)NH, $R^{15}$OC(O)NH, $R^{15}$NHC(O)NH, $(C_1-C_6)$alkyl-S(O)$_m$, $(C_1-C_6)$alkyl-S(O)$_m$—$(C_1-C_6)$alkyl, $R^{15}R^{16}$NS(O)$_m$, $R^{15}R^{16}$NS(O)$_m(C_1-C_6)$alkyl, $R^{15}$S(O)$_m R^{16}$N, $R^{15}$S(O)$_m R^{16}$N$(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each hydrogen.

10. A compound of the Formula I;

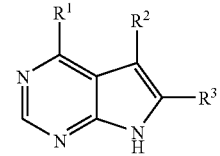

or a pharmaceutically acceptable salt thereof; wherein
$R^1$ is a group of the formula

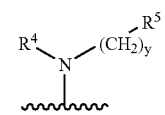

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$ amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}$N—CO—O—, $R^{15}R^{16}$N—CO—$(C_1-C_6)$alkyl, $(C_1-C_6)$alkyl-S(O)$_m$, $R^{15}R^{16}$NS(O)$_m$, $R^{15}R^{16}$NS(O)$_m(C_1-C_6)$alkyl, $R^{15}$S(O)$_m R^{16}$N, $R^{15}$S(O)$_m R^{16}$N$(C_1-C_6)$alkyl wherein m is 0, 1 or 2 and $R^{15}$ and $R^{16}$ are each independently selected from hydrogen or $(C_1-C_6)$alkyl; or a group of the formula

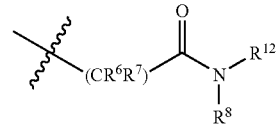

wherein $R^6$, $R^7$, and $R^8$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$ amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-$S(O)_m$, $(C_1-C_6)$alkyl-$S(O)_m$-$(C_1-C_6)$alkyl, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each hydrogen.

11. A compound of the Formula I;

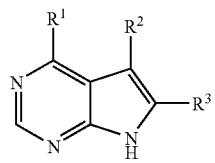

or a pharmaceutically acceptable salt thereof; wherein $R^1$ is a group of the formula

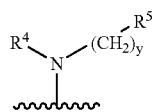

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $C_1-C_6$ acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$ amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $(C_1-C_6)$alkyl-$S(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula

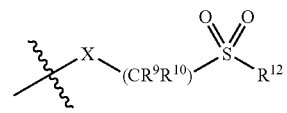

wherein X is $S(O)_n$ wherein n is 0, 1 or 2;

$R^9$ and $R^{10}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl $(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-$S(O)_m$, $(C_1-C_6)$alkyl-$S(O)_m$-$(C_1-C_6)$alkyl, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each hydrogen.

12. A compound of the Formula I;

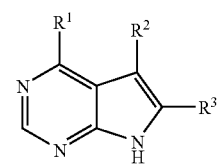

or a pharmaceutically acceptable salt thereof; wherein $R^1$ is a group of the formula

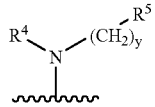

wherein y is 0, 1 or 2;

$R^4$ selected from the group consisting of hydrogen, $(C_1$-$C_6)$alkyl, $(C_1$-$C_6)$alkylsulfonyl, $(C_2$-$C_6)$alkenyl, $(C_2$-$C_6)$alkynyl wherein the alkyl, alkenyl and alkynyl groups are optionally substituted by deuterium, hydroxy, amino, trifluoromethyl, $(C_1$-$C_4)$alkoxy, $(C_1$-$C_6)$acyloxy, $(C_1$-$C_6)$alkylamino, $((C_1$-$C_6)$alkyl$)_2$amino, cyano, nitro, $(C_2$-$C_6)$alkenyl, $(C_2$-$C_6)$alkynyl or $(C_1$-$C_6)$acylamino; or $R^4$ is $(C_3$-$C_{10})$cycloalkyl wherein the cycloalkyl group is optionally substituted by deuterium, hydroxy, amino, trifluoromethyl, $(C_1$-$C_6)$acyloxy, $(C_1$-$C_6)$acylamino, $(C_1$-$C_6)$alkylamino, $((C_1$-$C_6)$alkyl$)_2$amino, cyano, cyano$(C_1$-$C_6)$alkyl, trifluoromethyl$(C_1$-$C_6)$alkyl, nitro, nitro$(C_1$-$C_6)$alkyl or $(C_1$-$C_6)$acylamino;

$R^5$ is a piperidinyl substituted by one to five carboxy, cyano, amino, deuterium, hydroxy, $(C_1$-$C_6)$alkyl, $(C_1$-$C_6)$alkoxy, halo, $(C_1$-$C_6)$acyl, $(C_1$-$C_6)$alkylamino, amino$(C_1$-$C_6)$alkyl, $(C_1$-$C_6)$alkoxy-CO—NH, $(C_1$-$C_6)$alkylamino-CO—, $(C_2$-$C_6)$alkenyl, $(C_2$-$C_6)$alkynyl, $(C_1$-$C_6)$alkylamino, amino$(C_1$-$C_6)$alkyl, hydroxy$(C_1$-$C_6)$alkyl, $(C_1$-$C_6)$alkoxy$(C_1$-$C_6)$alkyl, $(C_1$-$C_6)$acyloxy $(C_1$-$C_6)$alkyl, nitro, cyano$(C_1$-$C_6)$alkyl, halo$(C_1$-$C_6)$alkyl, nitro$(C_1$-$C_6)$alkyl, trifluoromethyl, trifluoromethyl$(C_1$-$C_6)$alkyl, $(C_1$-$C_6)$acylamino, $C_1$-$C_6)$acylamino$(C_1$-$C_6)$alkyl, $(C_1$-$C_6)$alkoxy$(C_1$-$C_6)$ acylamino, amino$(C_1$-$C_6)$acyl, amino$(C_1$-$C_6)$acyl$(C_1$-$C_6)$alkyl, $(C_1$-$C_6)$alkylamino$(C_1$-$C_6)$acyl, $((C_1$-$C_6)$alkyl$)_2$amino$(C_1$-$C_6)$acyl, $R^{15}R^{16}N$—CO—O—, $R^{15}R^{16}N$—CO—$(C_1$-$C_6)$alkyl, $(C_1$-$C_6)$alkyl-S(O)$_m$, $R^{15}R^{16}NS(O)_m$, $R^{15}R^{16}NS(O)_m(C_1$-$C_6)$alkyl, $R^{15}S(O)_m R^{16}N$, $R^{15}S(O)_m R^{16}N(C_1$-$C_6)$alkyl wherein m is 0, 1 or 2 and $R^{15}$ and $R^{16}$ are each independently selected from hydrogen or $(C_1$-$C_6)$alkyl; or a group of the formula

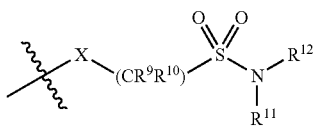

wherein X is $S(O)_n$ wherein n is 0, 1 or 2;

$R^9$, $R^{10}$ and $R^{11}$ are each independently selected from the group consisting of hydrogen or $(C_1$-$C_6)$alkyl optionally substituted by deuterium, hydroxy, amino, trifluoromethyl, $(C_1$-$C_6)$acyloxy, $(C_1$-$C_6)$acylamino, $(C_1$-$C_6)$alkylamino, $((C_1$-$C_6)$alkyl$)_2$amino, cyano, cyano$(C_1$-$C_6)$alkyl, trifluoromethyl$(C_1$-$C_6)$alkyl, nitro, nitro$(C_1$-$C_6)$alkyl or $(C_1$-$C_6)$acylamino;

$R^{12}$ is carboxy, cyano, amino, oxo, deuterium, hydroxy, trifluoromethyl, $(C_1$-$C_6)$alkyl, trifluoromethyl$(C_1$-$C_6)$alkyl, $(C_1$-$C_6)$alkoxy, halo, $(C_1$-$C_6)$acyl, $(C_1$-$C_6)$alkylamino, $((C_1$-$C_6)$alkyl$)_2$amino, amino$(C_1$-$C_6)$alkyl, $(C_1$-$C_6)$alkoxy-CO—NH, $(C_1$-$C_6)$alkylamino-CO—, $(C_2$-$C_6)$alkenyl, $(C_2$-$C_6)$alkynyl, $(C_1$-$C_6)$alkylamino, hydroxy$(C_1$-$C_6)$alkyl, $(C_1$-$C_6)$alkoxy$(C_1$-$C_6)$alkyl, $(C_1$-$C_6)$acyloxy$(C_1$-$C_6)$alkyl, nitro, cyano$(C_1$-$C_6)$alkyl, halo$(C_1$-$C_6)$alkyl, nitro$(C_1$-$C_6)$alkyl, trifluoromethyl, trifluoromethyl$(C_1$-$C_6)$alkyl, $(C_1$-$C_6)$acylamino, $(C_1$-$C_6)$acylamino$(C_1$-$C_6)$alkyl, $(C_1$-$C_6)$alkoxy$(C_1$-$C_6)$acylamino, amino$(C_1$-$C_6)$acyl, amino$(C_1$-$C_6)$acyl$(C_1$-$C_6)$alkyl, $(C_1$-$C_6)$alkylamino$(C_1$-$C_6)$acyl, $((C_1$-$C_6)$alkyl$)_2$amino$(C_1$-$C_6)$acyl, $R^{15}R^{16}N$—CO—O—, $R^{15}R^{16}N$—CO—$(C_1$-$C_6)$alkyl, $R^{15}C(O)NH$, $R^{15}OC(O)NH$, $R^{15}NHC(O)NH$, $(C_1$-$C_6)$alkyl-S(O)$_m$, $(C_1$-$C_6)$alkyl-S(O)$_m$-$(C_1$-$C_6)$alkyl, $R^{15}R^{16}NS(O)_m$, $R^{15}R^{16}NS(O)_m(C_1$-$C_6)$alkyl, $R^{15}S(O)_m R^{16}N$, $R^{15}S(O)_m R^{16}N(C_1$-$C_6)$alkyl wherein m is 0, 1 or 2 and $R^{15}$ and $R^{16}$ are each independently selected from hydrogen or $(C_1$-$C_6)$alkyl;

$R^2$ and $R^3$ are each hydrogen.

13. A compound of the Formula I;

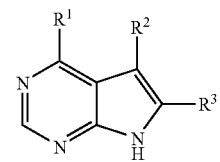

or a pharmaceutically acceptable salt thereof; wherein $R^1$ is a group of the formula

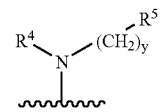

wherein y is 0, 1 or 2;

$R^4$ is selected from the group consisting of hydrogen, $(C_1$-$C_6)$alkyl, $(C_1$-$C_6)$alkylsulfonyl, $(C_2$-$C_6)$alkenyl, $(C_2$-$C_6)$alkynyl wherein the alkyl, alkenyl and alkynyl groups are optionally substituted by deuterium, hydroxy, amino, trifluoromethyl, $(C_1$-$C_4)$alkoxy, $(C_1$-$C_6)$acyloxy, $(C_1$-$C_6)$alkylamino, $((C_1$-$C_6)$alkyl$)_2$amino, cyano, nitro, $(C_2$-$C_6)$alkenyl, $(C_2$-$C_6)$alkynyl or $(C_1$-$C_6)$acylamino; or $R^4$ is $(C_3$-$C_{10})$cycloalkyl wherein the cycloalkyl group is optionally substituted by deuterium, hydroxy, amino, trifluoromethyl, $(C_1$-$C_6)$acyloxy, $(C_1$-$C_6)$acylamino, $(C_1$-$C_6)$alkylamino, $((C_1$-$C_6)$alkyl$)_2$amino, cyano, cyano$(C_1$-$C_6)$alkyl, trifluoromethyl$(C_1$-$C_6)$alkyl, nitro, nitro$(C_1$-$C_6)$alkyl or $(C_1$-$C_6)$acylamino;

$R^5$ is a piperidinyl substituted by one to five carboxy, cyano, amino, deuterium, hydroxy, $(C_1$-$C_6)$alkyl, $(C_1$-$C_6)$alkoxy, halo, $(C_1$-$C_6)$acyl, $(C_1$-$C_6)$alkylamino, amino$(C_1$-$C_6)$alkyl, $(C_1$-$C_6)$alkoxy-CO—NH, $(C_1$-$C_6)$alkylamino-CO—, $(C_2$-$C_6)$alkenyl, $(C_2$-$C_6)$alkynyl, $(C_2$-$C_6)$alkylamino, amino$(C_1$-$C_6)$alkyl, hydroxy$(C_1$-$C_6)$alkyl, $(C_1$-$C_6)$alkoxy$(C_1$-$C_6)$alkyl, $(C_1$-$C_6)$acyloxy $(C_1$-$C_6)$alkyl, nitro, cyano$(C_1$-$C_6)$alkyl, halo$(C_1$-$C_6)$alkyl, nitro$(C_1$-$C_6)$alkyl, trifluoromethyl, trifluoromethyl$(C_1$-$C_6)$alkyl, $(C_1$-$C_6)$acylamino, $(C_1$-$C_6)$acylamino$(C_1$-$C_6)$alkyl, $(C_1$-$C_6)$alkoxy$(C_1$-$C_6)$acylamino, amino$(C_1$-$C_6)$acyl, amino$(C_1$-$C_6)$acyl$(C_1$-$C_6)$alkyl, $(C_1$-$C_6)$alkylamino$(C_1$-$C_6)$acyl, $((C_1$-$C_6)$alkyl$)_2$amino$(C_1$-$C_6)$acyl, $R^{15}R^{16}N$—CO—O—, $R^{15}R^{16}N$—CO—$(C_1$-$C_6)$alkyl, $(C_1$-$C_6)$alkyl-S(O)$_m$, $R^{15}R^{16}NS(O)_m$, $R^{15}R^{16}NS(O)_m(C_1$-$C_6)$alkyl, $R^{15}S(O)_m R^{16}N$, $R^{15}S(O)_m R^{16}N(C_1$-$C_6)$alkyl wherein m is 0, 1 or 2 and $R^{15}$ and $R^{16}$ are each independently selected from hydrogen or $(C_1$-$C_6)$alkyl; or a group of the formula

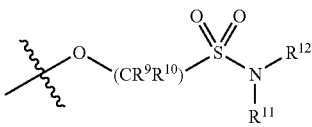

wherein $R^9$, $R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-$S(O)_m$, $(C_1-C_6)$alkyl-$S(O)_m$-$(C_1-C_6)$alkyl, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each hydrogen.

14. A compound of the Formula I;

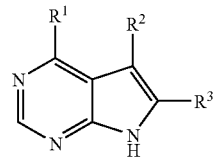

I or a pharmaceutically acceptable salt thereof; wherein
$R^1$ is a group of the formula

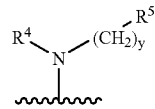

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is a piperidinyl substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $(C_1-C_6)$alkyl-$S(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula

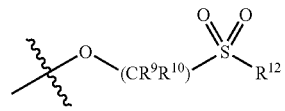

wherein $R^9$ and $R^{10}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-$S(O)_m$, $(C_1-C_6)$alkyl-$S(O)_m$-$(C_1-C_6)$alkyl, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each hydrogen.

15. A compound of the Formula I;

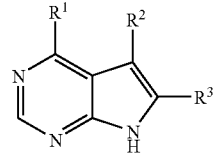

or a pharmaceutically acceptable salt thereof; wherein
R$^1$ is a group of the formula

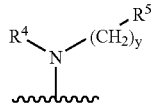

wherein y is 0, 1 or 2;
R$^4$ is selected from the group consisting of hydrogen, (C$_1$-C$_6$)alkyl, (C$_1$-C$_6$)alkylsulfonyl, (C$_2$-C$_6$)alkenyl, (C$_2$-C$_6$)alkynyl wherein the alkyl, alkenyl and alkynyl groups are optionally substituted by deuterium, hydroxy, amino, trifluoromethyl, (C$_1$-C$_4$)alkoxy, (C$_1$-C$_6$)acyloxy, (C$_1$-C$_6$)alkylamino, ((C$_1$-C$_6$)alkyl)$_2$amino, cyano, nitro, (C$_2$-C$_6$)alkenyl, (C$_2$-C$_6$)alkynyl or (C$_1$-C$_6$)acylamino; or R$^4$ is (C$_3$-C$_{10}$)cycloalkyl wherein the cycloalkyl group is optionally substituted by deuterium, hydroxy, amino, trifluoromethyl, (C$_1$-C$_6$)acyloxy, (C$_1$-C$_6$)acylamino, (C$_1$-C$_6$)alkylamino, ((C$_1$-C$_6$)alkyl)$_2$amino, cyano, cyano(C$_1$-C$_6$)alkyl, trifluoromethyl(C$_1$-C$_6$)alkyl, nitro, nitro(C$_1$-C$_6$)alkyl or (C$_1$-C$_6$)acylamino;
R$^5$ is a piperidinyl substituted by one to five carboxy, cyano, amino, deuterium, hydroxy, (C$_1$-C$_6$)alkyl, (C$_1$-C$_6$)alkoxy, halo, (C$_1$-C$_6$)acyl, (C$_1$-C$_6$)alkylamino, amino(C$_1$-C$_6$)alkyl, (C$_1$-C$_6$)alkoxy-CO—NH, (C$_1$-C$_6$)alkylamino-CO—, (C$_2$-C$_6$)alkenyl, (C$_2$-C$_6$)alkynyl, (C$_1$-C$_6$)alkylamino, amino(C$_1$-C$_6$)alkyl, hydroxy(C$_1$-C$_6$)alkyl, (C$_1$-C$_6$)alkoxy(C$_1$-C$_6$)alkyl, (C$_1$-C$_6$)acyloxy (C$_1$-C$_6$)alkyl, nitro, cyano(C$_1$-C$_6$)alkyl, halo(C$_1$-C$_6$)alkyl, nitro(C$_1$-C$_6$)alkyl, trifluoromethyl, trifluoromethyl(C$_1$-C$_6$)alkyl, (C$_1$-C$_6$)acylamino, (C$_1$-C$_6$)acylamino(C$_1$-C$_6$)alkyl, (C$_1$-C$_6$)alkoxy(C$_1$-C$_6$)acylamino, amino(C$_1$-C$_6$)acyl, amino(C$_1$-C$_6$)acyl(C$_1$-C$_6$)alkyl, (C$_1$-C$_6$)alkylamino(C$_1$-C$_6$)acyl, ((C$_1$-C$_6$)alkyl)$_2$amino(C$_1$-C$_6$)acyl, R$^{15}$R$^{16}$N—CO—O—, R$^{15}$R$^{16}$N—CO—(C$_1$-C$_6$)alkyl, (C$_1$-C$_6$)alkyl-S(O)$_m$, R$^{15}$R$^{16}$NS (O)$_m$, R$^{15}$R$^{16}$NS(O)$_m$(C$_1$C$_6$)alkyl, R$^{15}$S(O)$_m$R$^{16}$N, R$^{15}$S(O)$_m$R$^{16}$N(C$_1$-C$_6$)alkyl wherein m is 0, 1 or 2 and R$^{15}$ and R$^{16}$ are each independently selected from hydrogen or (C$_1$-C$_6$)alkyl; or a group of the formula

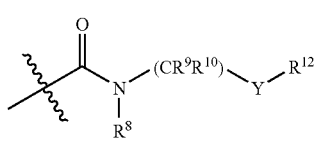

wherein Y is S(O)$_n$ wherein n is 0, 1 or 2;
R$^8$, R$^9$, and R$^{10}$ are each independently selected from the group consisting of hydrogen or (C$_1$-C$_6$)alkyl optionally substituted by deuterium, hydroxy, amino, trifluoromethyl, (C$_1$-C$_6$)acyloxy, (C$_1$-C$_6$)acylamino, (C$_1$-C$_6$)alkylamino, ((C$_1$-C$_6$)alkyl)$_2$amino, cyano, cyano(C$_1$-C$_6$)alkyl, trifluoromethyl(C$_1$-C$_6$)alkyl, nitro, nitro(C$_1$-C$_6$)alkyl or (C$_1$-C$_6$)acylamino;

R$^{12}$ is carboxy, cyano, amino, oxo, deuterium, hydroxy, trifluoromethyl, (C$_1$-C$_6$)alkyl, trifluoromethyl(C$_1$-C$_6$)alkyl, (C$_1$-C$_6$)alkoxy, halo, (C$_1$-C$_6$)acyl, (C$_1$-C$_6$)alkylamino, ((C$_1$-C$_6$)alkyl)$_2$amino, amino(C$_1$-C$_6$)alkyl, (C$_1$-C$_6$)alkoxy-CO—NH, (C$_1$-C$_6$)alkylamino-CO—, (C$_2$-C$_6$)alkenyl, (C$_2$-C$_6$)alkynyl, (C$_1$-C$_6$)alkylamino, hydroxy(C$_1$-C$_6$)alkyl, (C$_1$-C$_6$)alkoxy(C$_1$-C$_6$)alkyl, (C$_1$-C$_6$)acyloxy(C$_1$-C$_6$)alkyl, nitro, cyano(C$_1$-C$_6$)alkyl, halo(C$_1$-C$_6$)alkyl, nitro(C$_1$-C$_6$)alkyl, trifluoromethyl, trifluoromethyl(C$_1$-C$_6$)alkyl, (C$_1$-C$_6$)acylamino, (C$_1$-C$_6$)acylamino(C$_1$-C$_6$)alkyl, (C$_1$-C$_6$)alkoxy(C$_1$-C$_6$)acylamino, amino(C$_1$-C$_6$)acyl, amino(C$_1$-C$_6$)acyl(C$_1$-C$_6$)alkyl, (C$_1$-C$_6$)alkylamino(C$_1$-C$_6$)acyl, ((C$_1$-C$_6$)alkyl)$_2$amino(C$_1$-C$_6$)acyl, R$^{15}$R$^{16}$N—CO—O—, R$^{15}$R$^{16}$N—CO—(C$_1$-C$_6$)alkyl, R$^{15}$C(O)NH, R$^{15}$OC(O)NH, R$^{15}$NHC(O)NH, (C$_1$-C$_6$)alkyl-S(O)$_m$, (C$_1$-C$_6$)alkyl-S(O)$_m$—(C$_1$-C$_6$)alkyl, R$^{15}$R$^{16}$NS(O)$_m$, R$^{15}$R$^{16}$NS (O)$_m$(C$_1$-C$_6$)alkyl, R$^{15}$S(O)$_m$R$^{16}$N, R$^{15}$S(O)$_m$R$^{16}$N(C$_1$-C$_6$)alkyl wherein m is 0, 1 or 2 and R$^{15}$ and R$^{16}$ are each independently selected from hydrogen or (C$_1$-C$_6$)alkyl;
R$^2$ and R$^3$ are each hydrogen.

16. A compound of the Formula I;

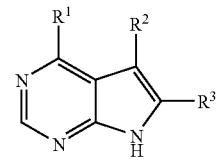

or a pharmaceutically acceptable salt thereof; wherein
R$^1$ is a group of the formula

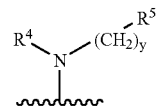

wherein y is 0, 1 or 2;
R$^4$ is selected from the group consisting of hydrogen, (C$_1$-C$_6$)alkyl, (C$_1$-C$_6$)alkylsulfonyl, (C$_2$-C$_6$)alkenyl, (C$_2$-C$_6$)alkynyl wherein the alkyl, alkenyl and alkynyl groups are optionally substituted by deuterium, hydroxy, amino, trifluoromethyl, (C$_1$-C$_4$)alkoxy, (C$_1$-C$_6$)acyloxy, (C$_1$-C$_6$)alkylamino, ((C$_1$-C$_6$)alkyl)$_2$amino, cyano, nitro, (C$_2$-C$_6$)alkenyl, (C$_2$-C$_6$)alkynyl or (C$_1$-C$_6$)acylamino; or R$^4$ is (C$_3$-C$_{10}$)cycloalkyl wherein the cycloalkyl group is optionally substituted by deuterium, hydroxy, amino, trifluoromethyl, (C$_1$-C$_6$)acyloxy, (C$_1$-C$_6$)acylamino, (C$_1$-C$_6$)alkylamino, ((C$_1$-C$_6$)alkyl)$_2$amino, cyano, cyano(C$_1$-C$_6$)alkyl, trifluoromethyl(C$_1$-C$_6$)alkyl, nitro, nitro(C$_1$-C$_6$)alkyl or (C$_1$-C$_6$)acylamino;
R$^5$ is a piperidinyl substituted by one to five carboxy, cyano, amino, deuterium, hydroxy, (C$_1$-C$_6$)alkyl, (C$_1$-C$_6$)alkoxy, halo, (C$_1$-C$_6$)acyl, (C$_1$-C$_6$)alkylamino, amino(C$_1$-C$_6$)alkyl, (C$_1$-C$_6$)alkoxy-CO—NH, (C$_1$-C$_6$)alkylamino-CO—, (C$_2$-C$_6$)alkenyl, (C$_2$-C$_6$)alkynyl, (C$_1$-C$_6$)alkylamino, amino(C$_1$-C$_6$)alkyl, hydroxy(C$_1$-C$_6$)alkyl, (C$_1$-C$_6$)alkoxy(C$_1$-C$_6$)alkyl, (C$_1$-C$_6$)acyloxy (C$_1$-C$_6$)alkyl, nitro, cyano(C$_1$-C$_6$)alkyl, halo(C$_1$-C$_6$)

alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$)alkyl, ($C_1$-$C_6$)alkylamino($C_1$-$C_6$)acyl, (($C_1$-$C_6$)alkyl)$_2$amino($C_1$-$C_6$)acyl, $R^{15}R^{16}N$—CO—O—, $R^{15}R^{16}N$—CO—($C_1$-$C_6$)alkyl, ($C_1$-$C_6$)alkyl-S(O)$_m$, $R^{15}R^{16}NS(O)_m$, $R^{15}R^{16}NS(O)_m$($C_1$-$C_6$)alkyl, $R^{15}S(O)_mR^{16}N$, $R^{15}S(O)_mR^{16}N$($C_1$-$C_6$)alkyl wherein m is 0, 1 or 2 and $R^{15}$ and $R^{16}$ are each independently selected from hydrogen or ($C_1$-$C_6$)alkyl; or a group of the formula

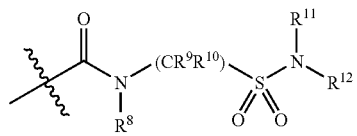

wherein $R^8$, $R^9$, $R^{10}$ and $R^{11}$ are each independently selected from the group consisting of hydrogen or ($C_1$-$C_6$)alkyl optionally substituted by deuterium, hydroxy, amino, trifluoromethyl, ($C_1$-$C_6$)acyloxy, ($C_1$-$C_6$)acylamino, ($C_1$-$C_6$) alkylamino, (($C_1$-$C_6$)alkyl)$_2$amino, cyano, cyano($C_1$-$C_6$) alkyl, trifluoromethyl($C_1$-$C_6$)alkyl, nitro, nitro($C_1$-$C_6$)alkyl or ($C_1$-$C_6$)acylamino;

$R^{12}$ is carboxy, cyano, amino, oxo, deuterium, hydroxy, trifluoromethyl, ($C_1$-$C_6$)alkyl, trifluoromethyl($C_1$-$C_6$) alkyl, ($C_1$-$C_6$)alkoxy, halo, ($C_1$-$C_6$)acyl, ($C_1$-$C_6$)alkylamino, (($C_1$-$C_6$)alkyl)$_2$amino, amino($C_1$-$C_6$)alkyl, ($C_1$-$C_6$)alkoxy-CO—NH, ($C_1$-$C_6$)alkylamino-CO—, ($C_2$-$C_6$)alkenyl, ($C_2$-$C_6$)alkynyl, ($C_1$-$C_6$)alkylamino, hydroxy($C_1$-$C_6$)alkyl, ($C_1$-$C_6$)alkoxy($C_1$-$C_6$)alkyl, ($C_1$-$C_6$)acyloxy($C_1$-$C_6$)alkyl, nitro, cyano($C_1$-$C_6$)alkyl, halo($C_1$-$C_6$)alkyl, nitro($C_1$-$C_6$)alkyl, trifluoromethyl, trifluoromethyl($C_1$-$C_6$)alkyl, ($C_1$-$C_6$)acylamino, ($C_1$-$C_6$)acylamino($C_1$-$C_6$)alkyl, ($C_1$-$C_6$)alkoxy($C_1$-$C_6$)acylamino, amino($C_1$-$C_6$)acyl, amino($C_1$-$C_6$)acyl($C_1$-$C_6$) alkyl, ($C_1$-$C_6$)alkylamino($C_1$-$C_6$)acyl, (($C_1$-$C_6$)alkyl)$_2$ amino($C_1$-$C_6$)acyl, $R^{15}R^{16}N$—CO—O—, $R^{15}R^{16}N$—CO—($C_1$-$C_6$)alkyl, $R^{15}C(O)NH$, $R^{15}OC(O)NH$, $R^{15}NHC(O)NH$, ($C_1$-$C_6$)alkyl-S(O)$_m$, ($C_1$-$C_6$)alkyl-S(O)$_m$—($C_1$-$C_6$)alkyl, $R^{15}R^{16}NS(O)_m$, $R^{15}R^{16}NS(O)_m$ ($C_1$-$C_6$)alkyl, $R^{15}S(O)_mR^{16}N$, $R^{15}S(O)_mR^{16}N$($C_1$-$C_6$) alkyl wherein m is 0, 1 or 2 and $R^{15}$ and $R^{16}$ are each independently selected from hydrogen or ($C_1$-$C_6$)alkyl; $R^2$ and $R^3$ are each hydrogen.

17. A compound selected from the group consisting of:
({4-Methyl-3-[methyl-(7H-pyrrolo[2,3-d]pyrimidin-4-yl)-amino]-piperidine-1-carbonyl}-amino)-acetic acid ethyl ester;
N-cyano-4-methyl-3-[methyl-(7H-pyrrolo[2,3-d]pyrimidin-4-yl)-amino]-N'-propyl-piperidine-1-carboxamidine; and
N-cyano-4,N',N'-Trimethyl-3-[methyl-(7H-pyrrolo[2,3-d]pyrimidin-4-yl)-amino]-piperidine-1-carboxamidine,
or a pharmaceutically acceptable salt thereof.

18. A compound selected from the group consisting of:
1-{4-Methyl-3-[methyl-(7H-pyrrolo[2,3-d]pyrimidin-4-yl)-amino]-piperidin-1-yl}-ethanone;
[1-(2-Amino-ethanesulfonyl)-4-methyl-piperidin-3-yl]-methyl-(7H-pyrrolo[2,3-d]pyrimidin-4-yl)-amine;
(1-Ethanesulfonyl-4-methyl-piperidin-3-yl)-methyl-(7H-pyrrolo[2,3-d]pyrimidin-4-yl)-amine;
[1-(Butane-1-sulfonyl)-4-methyl-piperidin-3-yl]-methyl-(7H-pyrrolo[2,3-d]pyrimidin-4-yl)-amine;
4-Methyl-3-[methyl-(7H-pyrrolo[2,3-d]pyrimidin-4-yl)-amino]-piperidine-1-carboxylic acid isobutyl ester;
N-(2-{4-Methyl-3-[methyl-(7H-pyrrolo[2,3-d]pyrimidin-4-yl)-amino]-piperidine-1-sulfonyl}-ethyl)-propionamide;
(2-{4-Methyl-3-[methyl-(7H-pyrrolo[2,3-d]pyrimidin-4-yl)-amino]-piperidine-1-sulfonyl}-ethyl)-carbamic acid methyl ester;
N-(2-{4-Methyl-3-[methyl-(7H-pyrrolo[2,3-d]pyrimidin-4-yl)-amino]-piperidine-1-sulfonyl}-ethyl)-isobutyramide;
(1-Methanesulfonyl-piperidin-3-yl)-methyl-(7H-pyrrolo[2,3-d]pyrimidin-4-yl)-amine;
(1-Ethanesulfonyl-piperidin-3-yl)-methyl-(7H-pyrrolo[2,3-d]pyrimidin-4-yl)-amine;
Methyl-[1-(propane-1-sulfonyl)-piperidin-3-yl]-(7H-pyrrolo[2,3-d]pyrimidin-4-yl)-amine;
[1-(Butane-1-sulfonyl)-piperidin-3-yl]-methyl-(7H-pyrrolo[2,3-d]pyrimidin-4-yl)-amine;
2,2-Dimethyl-N-(2-{4-methyl-3-[methyl-(7H-pyrrolo[2,3-d]pyrimidin-4-yl)-amino]-piperidine-1-sulfonyl}-ethyl)-propionamide;
(3-{4-Methyl-3-[methyl-(7H-pyrrolo[2,3-d]pyrimidin-4-yl)-amino]-piperidin-1-yl}-3-oxo-propyl)-carbamic acid tert-butyl ester;
3-Amino-1-{4-methyl-3-[methyl-(7H-pyrrolo[2,3-d]pyrimidin-4-yl)-amino]-piperidin-1-yl}-propan-1-one;
2-Methoxy-1-{4-methyl-3-[methyl-(7H-pyrrolo[2,3-d]pyrimidin-4-yl)-amino]-piperidin-1-yl}-ethanone;
2-Dimethylamino-1-{4-methyl-3-[methyl-(7H-pyrrolo[2,3-d]pyrimidin-4-yl)-amino]-piperidin-1-yl}-ethanone;
(3-{4-Methyl-3-[methyl-(7H-pyrrolo[2,3-d]pyrimidin-4-yl)-amino]-piperidin-1-yl}-3-oxo-propyl)-carbamic acid tert-butyl ester;
N-(2-{4-Methyl-3-[methyl-(7H-pyrrolo[2,3-d]pyrimidin-4-yl)-amino]-piperidin-1-yl}-2-oxo-ethyl)-acetamide;
3-Ethoxy-1-{4-methyl-3-[methyl-(7H-pyrrolo[2,3-d]pyrimidin-4-yl)-amino]-piperidin-1-yl}-propan-1-one;
4-Methyl-3-[methyl-(7H-pyrrolo[2,3-d]pyrimidin-4-yl)-amino]-piperidine-1-carboxylic acid methylamide;
4-Methyl-3-4methyl-(7H-pyrrolo[2,3-d]pyrimidin-4-yl)-amino]-piperidine-1-carboxylic acid diethylamide;
Methyl-[4-methyl-1-(2-methylamino-ethanesulfonyl)-piperidin-3-yl]-(7H-pyrrolo[2,3-d]pyrimidin-4-yl)-amine,
or a pharmaceutically acceptable salt thereof.

* * * * *